US012642567B2

(12) United States Patent
Brockman et al.

(10) Patent No.: US 12,642,567 B2
(45) Date of Patent: Jun. 2, 2026

(54) CURABLE MATERIAL DISPENSING SYSTEM AND METHODS OF OPERATING AND PACKAGING THE SAME

(71) Applicant: Stryker Corporation, Kalamazoo, MI (US)

(72) Inventors: Christopher Brockman, Kalamazoo, MI (US); Gabriel Harshman, Portage, MI (US)

(73) Assignee: Stryker Corporation, Portage, MI (US)

( * ) Notice: Subject to any disclaimer, the term of this patent is extended or adjusted under 35 U.S.C. 154(b) by 368 days.

(21) Appl. No.: 18/111,956

(22) Filed: Feb. 21, 2023

(65) Prior Publication Data

US 2023/0200875 A1　　Jun. 29, 2023

Related U.S. Application Data

(63) Continuation of application No. 17/045,653, filed as application No. PCT/US2019/026973 on Apr. 11, 2019, now Pat. No. 11,607,258.

(Continued)

(51) Int. Cl.
*A61B 17/88*　　(2006.01)
*B05C 17/01*　　(2006.01)

(52) U.S. Cl.
CPC ...... *A61B 17/8822* (2013.01); *A61B 17/8816* (2013.01); *B05C 17/0133* (2013.01)

(58) Field of Classification Search
CPC ............ A61B 17/8822; A61B 17/8816; A61B 17/8825; A61B 17/8833; A61B 17/8805; A61B 2090/031; B05C 17/0133
See application file for complete search history.

(56) References Cited

U.S. PATENT DOCUMENTS 4,466,523 A * 8/1984 De Carolis ........... B25B 13/462
　　　　　　　　　　　　　　　　　　　81/62
4,479,781 A * 10/1984 Herold .............. B05C 17/00593
　　　　　　　　　　　　　　　　　　　433/90

(Continued)

FOREIGN PATENT DOCUMENTS

WO　　2008045329 A2　　4/2008
WO　　2008080590 A1　　7/2008

(Continued)

OTHER PUBLICATIONS

International Search Report for Application No. PCT/US2019/026973 dated Jun. 25, 2019, 4 pages.

*Primary Examiner* — Amy R Sipp
(74) *Attorney, Agent, or Firm* — Howard & Howard Attorneys PLLC

(57) ABSTRACT

A system for dispensing curable material. A lead screw is rotatably fixed relative to a first control surface and includes external threads. A locking nut includes internal threads threadably engaging the external threads. An engagement feature of the locking nut is adapted to be selectively engaged with an actuator having a second control surface. The threads provide for rotation of the locking nut about a translation axis when the actuator is in a disengaged position. Rotation of the locking nut permits the lead screw to move proximally along the axis and the compressed curable material to at least partially decompress within a dispensing volume. The threads further provide for distal advancement of the lead screw along the axis when the actuator is in an engaged position rotatably fixing the locking nut about the axis. Methods for operating and packaging the curable material dispensing system are also described.

16 Claims, 16 Drawing Sheets

Related U.S. Application Data

(60) Provisional application No. 62/656,033, filed on Apr. 11, 2018.

(56) References Cited

U.S. PATENT DOCUMENTS

| | | | |
|---|---|---|---|
| 4,498,904 | A | 2/1985 | Turner et al. |
| 5,000,721 | A * | 3/1991 | Williams ................ F16D 7/048 464/37 |
| 5,603,701 | A | 2/1997 | Fischer |
| 6,547,432 | B2 | 4/2003 | Coffeen et al. |
| 6,736,537 | B2 | 5/2004 | Coffeen et al. |
| 7,134,782 | B2 | 11/2006 | Coffeen et al. |
| 7,270,667 | B2 | 9/2007 | Faccioli et al. |
| 7,306,361 | B2 | 12/2007 | Coffeen et al. |
| 7,320,540 | B2 | 1/2008 | Coffeen |
| 7,371,241 | B2 | 5/2008 | Evans et al. |
| 8,038,682 | B2 | 10/2011 | McGill et al. |
| 8,128,275 | B2 | 3/2012 | Axelsson et al. |
| 8,506,572 | B2 | 8/2013 | Evans et al. |
| 8,568,420 | B2 | 10/2013 | O'Halloran et al. |
| 8,603,096 | B2 | 12/2013 | Agard et al. |
| 8,876,834 | B2 | 11/2014 | Bonnin et al. |
| 9,060,826 | B2 | 6/2015 | Coale |
| 9,393,062 | B2 | 7/2016 | O'Halloran et al. |
| 2004/0204715 | A1 * | 10/2004 | Evans ................ A61B 17/8819 606/92 |
| 2004/0260304 | A1 | 12/2004 | Faccioli et al. |
| 2006/0131344 | A1 * | 6/2006 | Brass ........................ F04B 9/14 222/390 |
| 2009/0270862 | A1 | 10/2009 | Arcenio |
| 2010/0275744 | A1 * | 11/2010 | Wengreen ............. B26B 19/046 81/477 |
| 2010/0282774 | A1 * | 11/2010 | Greter ............... B05C 17/00553 222/137 |
| 2012/0195157 | A1 | 8/2012 | McKay |
| 2013/0030381 | A1 | 1/2013 | Langley et al. |
| 2013/0079786 | A1 * | 3/2013 | Bonnin ............. A61B 17/8827 606/94 |
| 2014/0366691 | A1 * | 12/2014 | Ivinson .................. A61B 90/03 81/475 |
| 2017/0065322 | A1 * | 3/2017 | Prado ................ A61B 17/8888 |
| 2017/0265920 | A1 | 9/2017 | Faccioli et al. |
| 2017/0265921 | A1 | 9/2017 | Faccioli et al. |
| 2017/0302479 | A1 | 10/2017 | Mysore Balasubramanya et al. |
| 2018/0028247 | A1 | 2/2018 | Giffard et al. |
| 2019/0038331 | A1 | 2/2019 | Purdy et al. |
| 2021/0113254 | A1 | 4/2021 | Brockman et al. |

FOREIGN PATENT DOCUMENTS

| | | |
|---|---|---|
| WO | 2016027176 A1 | 2/2016 |
| WO | 2018145116 A1 | 8/2018 |
| WO | 2018156755 A1 | 8/2018 |

* cited by examiner

CURABLE MATERIAL DISPENSING SYSTEM AND METHODS OF OPERATING AND PACKAGING THE SAME

CROSS REFERENCE TO RELATED APPLICATIONS

This is a continuation of copending U.S. application Ser. No. 17/045,653, filed Oct. 6, 2020, which is a United States national entry of International Patent Application No. PCT/US2019/026973, filed on Apr. 11, 2019, which claims the benefit of and priority to U.S. Provisional Patent Application No. 62/656,033, filed on Apr. 11, 2018, the entire contents of each being hereby incorporated by reference.

BACKGROUND

Certain surgical procedures include the placement of curable material within bony anatomy. For example, a vertebroplasty procedure involves directing an access cannula directed through the cortical bone of a vertebral body to within the cancellous region of the vertebral body. A dispensing system is coupled to the access cannula, and the system is operated to dispense the curable material through the access cannula and into the cancellous region. Known dispensing systems have several shortcomings.

SUMMARY

In certain implementations, a system for dispensing curable material includes a chamber defining a dispensing volume that is adapted to dispense the curable material through a distal outlet in communication with the dispensing volume. A first control surface is adapted to receive a primary input force from a user, and a lead screw is rotatably fixed relative to the first control surface. The lead screw includes a proximal end, a distal end, external threads at least partially disposed between the proximal and distal ends, and a translation axis defined between the proximal and distal ends. A plunger is coupled to the lead screw with the plunger disposed within the dispensing volume. The plunger is adapted to be advanced distally along the translation axis to compress the curable material within the dispensing volume in response to the first control surface receiving the primary input force. A locking nut includes internal threads threadably engaging the external threads of the lead screw, and an engagement feature. The system also includes an actuator having a second control surface that is adapted to receive a secondary input force from the user to engage the actuator and the engagement feature of the locking nut in an engaged position and disengage the actuator and the engagement feature of the locking nut in a disengaged position. The internal threads of the locking nut and the external threads of the lead screw are configured to provide for rotation of the locking nut about the translation axis when the actuator is in the disengaged position to permit the plunger to move proximally along the translation axis and permit the compressed curable material to at least partially decompress within the dispensing volume.

In certain implementations, a system for dispensing curable material includes a housing, and a chamber coupled to the housing. The chamber defines a dispensing volume that is adapted to dispense the curable material. A first control surface is coupled to the housing and adapted to receive a primary input force from a user. A lead screw is rotatably fixed relative to the first control surface with the lead screw including a proximal end, a distal end, external threads at least partially disposed between the proximal and distal ends, and a translation axis defined between the proximal and distal ends. A plunger is coupled to the distal end of the lead screw. The system includes a locking nut having internal threads threadably engaging the external threads of the lead screw, and an engagement feature. An actuator is coupled to the housing and includes a second control surface. The second control surface is adapted to receive a secondary input force from the user to engage the actuator and the engagement feature of the locking nut in an engaged position and disengage the actuator and the engagement feature of the locking nut in a disengaged position. The locking nut is adapted to be rotatably fixed relative to the housing and prevent rotation of the locking nut about the translation axis when the actuator is in the engaged position such that the internal threads of the locking nut and the external threads of the lead screw provide for distal advancement the lead screw and the plunger along the translation axis to compress the curable material within the dispensing volume in response to the first control surface receiving the primary input force.

In certain implementations, a system for dispensing curable material includes a housing, and a chamber coupled to the housing. The chamber defines a dispensing volume that is adapted to dispense the curable material. A first control surface coupled to the housing and adapted to receive a primary input force from a user. The system includes a locking nut disposed within the housing and includes internal threads. A lead screw is rotatably fixed relative to the first control surface with the lead screw includes a proximal end, a distal end, external threads at least partially disposed between the proximal and distal ends, and a translation axis defined between the proximal and distal ends. Engagement between the external threads of lead screw and the internal threads of the locking nut adapted to provide for movement of the lead screw along the translation axis to compress the curable material within the dispensing volume in response to the first control surface receiving the primary input force in a first direction. A defeatable unidirectional mechanism is operably coupling the first control surface and the housing. The defeatable unidirectional mechanism is adapted to permit for distal advancement of the lead screw in response to the first control surface receiving the primary input force includes a first torque input below a torque threshold, and permit proximal movement of the lead screw with rotation of the first control surface about the translation axis in a second direction opposite the first direction in response to the first control surface receiving a second torque input opposite the first torque input and at least equal to the torque threshold.

In certain implementations, a system for dispensing curable material, the system includes a chamber defining a dispensing volume for dispensing the curable material. A lead screw is rotatably fixed relative to a first control surface with the lead screw includes a proximal end, a distal end, external threads at least partially disposed between the proximal and distal ends, and a translation axis defined between the proximal and distal ends. A locking nut includes internal threads threadably engaging the external threads of the lead screw. The internal threads of the locking nut and the external threads of the lead screw are defined by a screw efficiency of greater than 50% such that the locking nut is adapted to rotate about the translation axis to permit the lead screw to translate proximally along the translation axis in response to proximal forces provided by the compressed curable material within the dispensing volume.

In certain implementations, a system for dispensing curable material includes a chamber defining a dispensing volume adapted to dispense the curable material. A first control surface is adapted to receive a primary input force from a user. A lead screw is rotatably fixed relative to the first control surface. The lead screw includes a proximal end, a distal end, external threads at least partially disposed between the proximal and distal ends, and a translation axis defined between the proximal and distal ends. The lead screw is adapted to be advanced distally along the translation axis to compress the curable material within the dispensing volume in response to the first control surface receiving the primary input force. A locking nut includes internal threads threadably engaging the external threads of the lead screw. The internal threads of the locking nut and the external threads of the lead screw are configured to provide for rotation of the locking nut about the translation axis in response to the lead screw translating proximally without rotation along the translation axis to permit the compressed curable material to at least partially decompress within the dispensing volume.

In certain implementations, a method for operating a curable material dispensing system includes applying a secondary input force to a second control surface to move the second control surface from a disengaged position to an engaged position. The second control surface is maintained in the engaged position against a force provided by a biasing member. With the second control surface maintained in the engaged position, a primary input force is provided to a first control surface to move a lead screw distally along a translation axis to compress curable material within a dispensing volume. The secondary input force provided to the second control surface is removed to permit the biasing member to move the second control surface from the engaged position to the disengaged position. The second control surface in the disengaged position provides for movement of the lead screw proximally along the translation axis to permit the compressed curable material to at least partially decompress within the dispensing volume.

In certain implementations, a method for operating a curable material dispensing system includes applying a primary input force to a first control surface while an actuator is biased into engagement with a locking nut to rotatably fix the locking nut about a translation axis. The threadable engagement provides for translation of the lead screw distally along the translation axis to compress curable material within a dispensing volume. A secondary input force is applied to a second control surface sufficient to overcome the force provided by a biasing member and move the actuator out of engagement from the locking nut and provide for rotation of the locking nut about the translation axis. The threadable engagement and the rotation of the locking nut permits translation of the lead screw proximally along the translation axis to permit the compressed curable material to at least partially decompress within the dispensing volume.

In certain implementations, a method for operating a curable material dispensing system includes providing packaging with dimensions sufficient to accommodate a curable material dispensing system. The curable material dispensing system is provided including a housing, a dispensing volume coupled to the housing. An extension tube is provided that includes a flexible tube rotatably coupled to a rotating coupler, and an elbow coupler coupled to the rotating coupler. The elbow coupler of the extension tube is coupled to a distal end of the dispensing volume, thereby establishing fluid communication between the flexible tube and the dispensing volume. The flexile tube is articulated relative to the dispensing volume about the elbow coupler to a packaging configuration in which the flexible tube and the dispensing volume are substantially parallel and the flexible tube is positioned towards the dispensing volume relative to the elbow coupler. Thereafter, the curable material dispensing system and the extension tube are positioned within the packaging in the packaging configuration.

BRIEF DESCRIPTION OF THE DRAWINGS

Advantages of the present disclosure will be readily appreciated as the same becomes better understood by reference to the following detailed description when considered in connection with the accompanying drawings.

DETAILED DESCRIPTION

Figure 1:
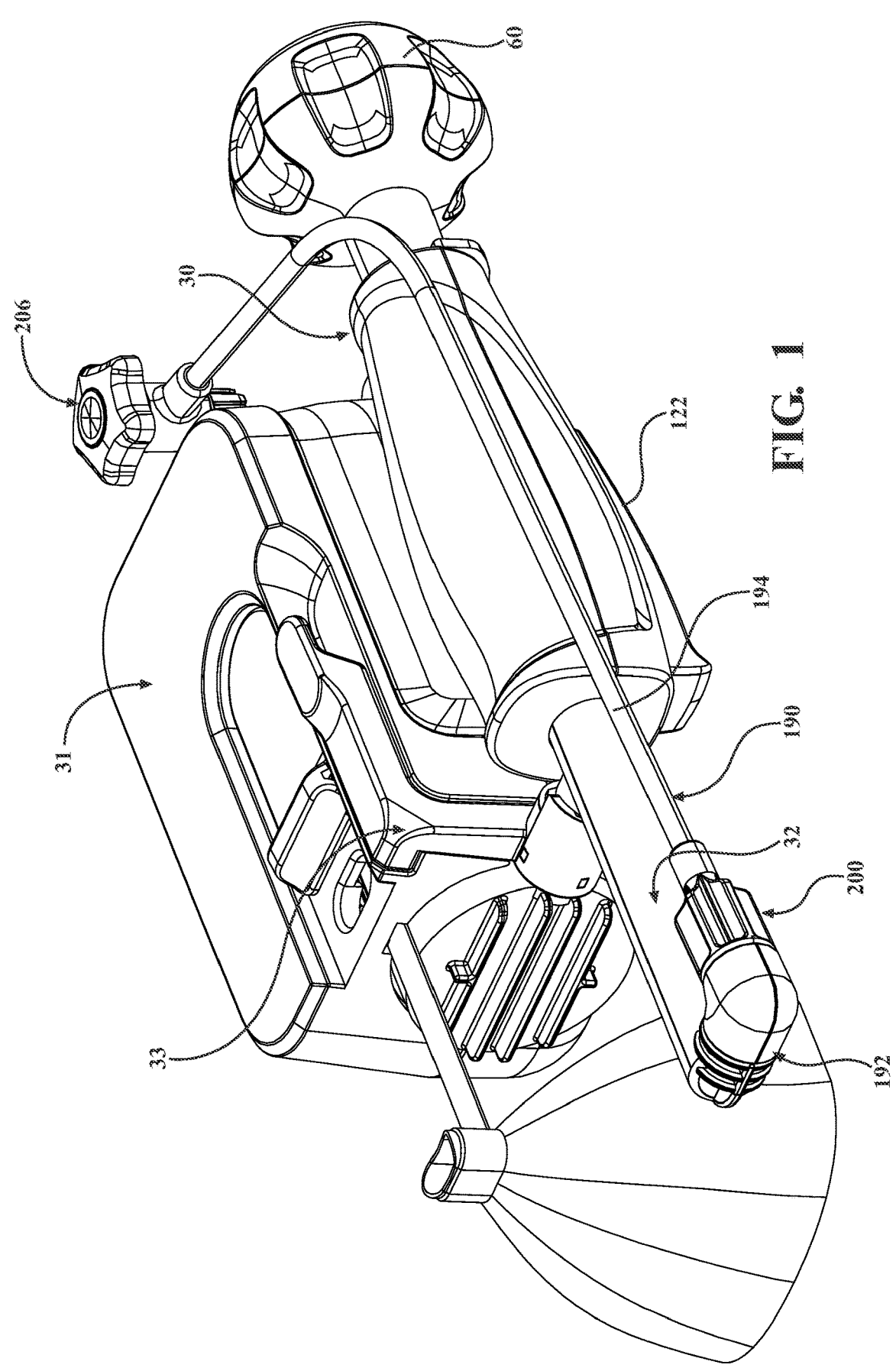
FIG. 1 is a perspective view of a curable material dispensing system removably coupled to a mixing and compression system.
Figure 2:
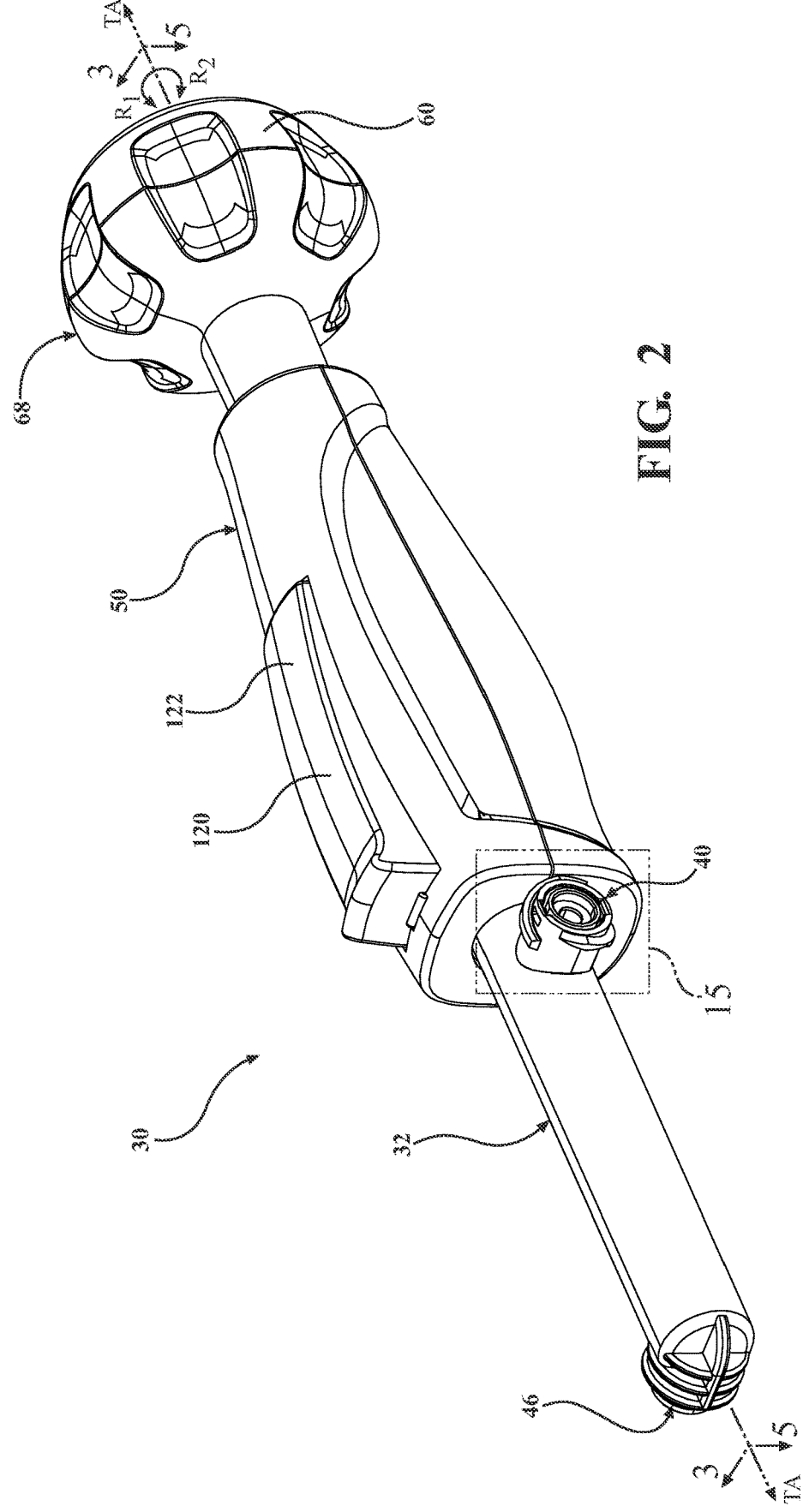
FIG. 2 is a perspective view of the curable material dispensing system.

FIGS. 1-6 show a system 30 for dispensing curable material. The system 30 may include a chamber 32 defining a dispensing volume 34 for receiving and dispensing the curable material. The curable material may be, for example, bone cement formed from mixing a powdered copolymer and a liquid monomer. In certain implementations, the chamber 32 may receive the pre-mixed curable material from a mixing and compression system 31 to which the system 30 is removably coupled. An exemplary mixing and compression system 31 suitable for the present application is disclosed in commonly owned International Publication No. 2008/08045329, the contents of which are hereby incorporated by reference in its entirety. Alternatively, it is contemplated that the chamber 32 may receive the powdered copolymer and/or the liquid monomer, and thereafter mix the contents within the dispensing volume 34 prior to dispensing the curable material in a manner to be described. Exemplary components suitable for the mixing the curable material within the dispensing volume 34 are disclosed in commonly owned U.S. Pat. Nos. 6,547,432; 6,736,537; 7,134,782; 7,306,361; 7,320,540, each of which is hereby incorporated by reference in its entirety.

Before the start of the surgical procedure, the inventors of the subject application have recognized that known systems may require an undue amount of valuable space within the surgical suite. The systems may also require assembly of a flexible tube that is ultimately coupled to the access cannula, further consuming time and resources that could be diverted to other tasks associated with the surgical procedure. Still further, during the surgical procedure fluoroscopy may be utilized visualize the curable material within the bony anatomy. Known dispensing systems may not provide adequate maneuverability of the physician about the surgical site while holding the dispensing system to avoid the radiation associated with fluoroscopic imaging. Perhaps most importantly, for any number of reasons during the surgical procedure, it may be desirable for the physician to immediately cease delivery of the curable material, for example, recognition of a surgical complication such as an excessive amount of highly pressurized curable material being introduced into the body. Many known dispensing systems are inadequate for this purpose, as the compressed curable material at least partially decompresses along a path of least resistance, namely, out the system and into the patient. This concept, known as "drool" results in additional curable material being delivered into the patient, contrary to the intentions of the physician, until pressure gradient between the dispensing volume and the surgical site is sufficiently reduced. With concurrent reference to FIG. 5, the exemplary chamber 32 includes a proximal end 36 and a distal outlet 38 positioned at least substantially opposite the proximal end 36. The distal outlet 38 is in communication with the dispensing volume 34. The chamber 32 may be elongate and substantially tubular in shape, as shown in FIGS. 1-5, or assume any suitable size and shape based on the design of the system 30 or demands of the surgical application.

Figure 15:
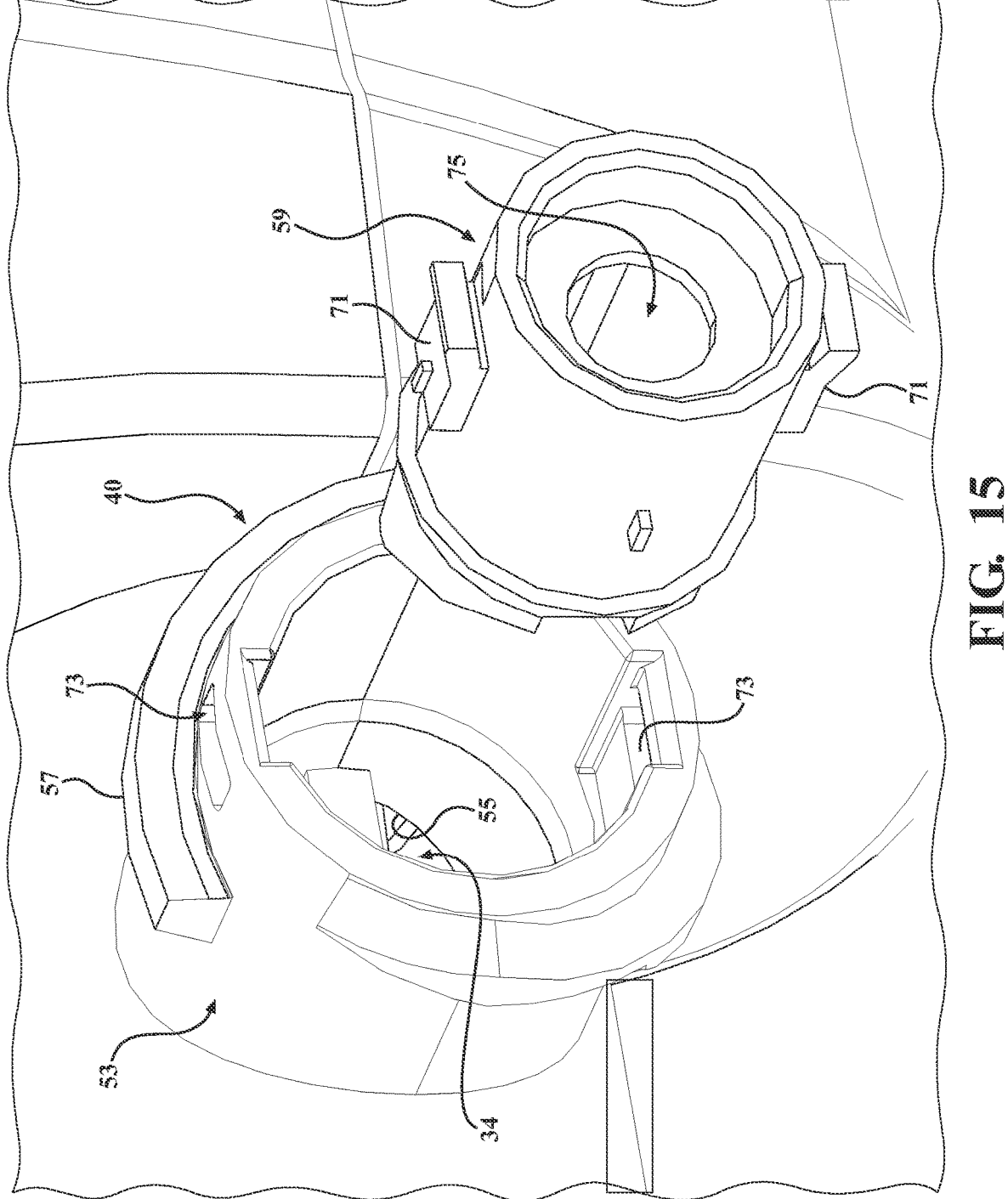
FIG. 15 is a detailed perspective view of a portion of the curable material dispensing system of FIG. 2 within box 15-15.

The chamber 32 may include an inlet port 40 at least initially in fluid communication with the dispensing volume 34. The inlet port 40 is adapted to be removably coupled with the mixing and compression system 31. The curable material passing through the inlet port 40 and into the dispensing volume 34 defines a transfer phase. During the transfer phase, the inlet port 40 is in fluid communication with the dispensing volume 34 and the distal outlet 38. With reference to FIG. 15, the inlet port 40 may include a neck portion 53 extending from the chamber 32. The neck portion 53 may define an aperture 55 in communication with the dispensing volume 34. The neck portion 53 may be tubular in shape and include at least one rib 57 extending radially outward. FIG. 15 shows two ribs 57 in a generally helical arrangement. The ribs 57 are configured to cooperate with complementary features of a release assembly 33 of the mixing and compression system 31 to draw the inlet port 40 into sealing engagement with an outlet port (not identified) of the mixing and compression system 31. A seal 59 may be at least partially disposed within the neck portion 53. The seal 59 may include coupling features 71 configured to engage complementary coupling features 73 of the neck portion 53 to axially retain the seal 59. FIG. 15 shows the coupling features 71 as deflectable fingers configured to resiliently deflect to engage openings at least partially forming the complementary coupling features 73. With the seal 59 coupled to the neck portion 53, a lumen 75 extending through the seal 59 is in selective communication with the dispensing volume 34.

Returning to FIGS. 2-5, during dispensing of the curable material from the distal outlet 38 in the manner to be described, a sealing interface 43 between the plunger 42 and the chamber 32 may move distal to the inlet port 40 with distal movement of the plunger 42, after which the inlet port 40 may no longer be considered in fluid communication with the dispensing volume 34 and the distal outlet 38. The sealing interface 43 may be defined between an outer surface of the plunger 42 and an inner surface of the chamber 32. The sealing interface 43 may be defined by a seal (not shown) coupled to the plunger 42. The seal may be an O-ring (uncoated or coated with a friction-reducing material) or other compression seal, or a dynamic seal. The dynamic seal, for example a feather tip seal, provides for a sealing force proportional to the force on the seal itself. As the plunger 42 moves relative to the chamber 32, friction at the sealing interface 43 may drop to near zero while sealing the curable material distal to the plunger 42. The sealing interface 43, whether or not defined by a discrete seal, is configured with minimal friction while maintaining the sealing properties between the plunger 42 and the chamber 32. Among additional advantages to be described, providing minimal friction at the sealing interface 43 facilitates a backdrivable system and improved feedback to the physician during operation of the curable material dispensing system 30.

A chamber mount 44 may be coupled to or integrally formed with the chamber 32 at or near the proximal end 36 to, among other things, secure the chamber 32 a housing 50. The chamber mount 44 may include opposing struts 45 extending laterally outward from the chamber 32 and adapted to be seated within correspondingly shaped slots 54 (one shown in FIG. 6) defined within the housing 50. The opposing struts 45 may also extend in a proximal-to-distal direction to a position proximal to the proximal end 36 of the chamber 32, and at least partially define a void 47 sized to accommodate several components of the system 30 to be described. The void 47 may be bound laterally by the opposing struts 45, and proximally by a proximal ring 49. Further, the void 47 may be bound distally by the proximal end 36 of the chamber 32. The void 47 may be open on sides not including the opposing struts 45. At least one of the opposing struts 45 may include an opening 51 sized to receive an engagement feature 123 of an actuator 120 such that a locking nut 90 disposed within the void 47 may be engaged by the actuator 120 in a manner to be described.

A distal coupler 46 of the chamber 32 is adapted to be removably coupled to an extension tube 190 (see FIG. 16) to be described. The extension tube 190 may be adapted to be coupled to a surgical instrument placed within the patient, such as an access cannula penetrating the bony anatomy. The distal coupler 46 may be a Luer fitting, a bayonet mount, or other suitable connection adapted to be removably receive an elbow coupler 192 of the extension tube 190 of the present disclosure, or a proximal end of a known tubular device.

The chamber 32 may be at least partially formed from translucent or transparent material such that the curable material (and the plunger 42) within the dispensing volume 34 is visible to the physician. Indicia (not shown) may be provided on the outer surface 52 of the chamber 32 to provide the physician with an amount of the curable material within the dispensing volume 34, and/or the amount of the curable material dispensed from the dispensing volume 34; i.e., based on a determined distance traveled by the plunger 42 within the dispensing volume 34. The indicia may be numerical graduations corresponding to a volume of the dispensing volume 34 (e.g., in cubic centimeters).

Figure 3:
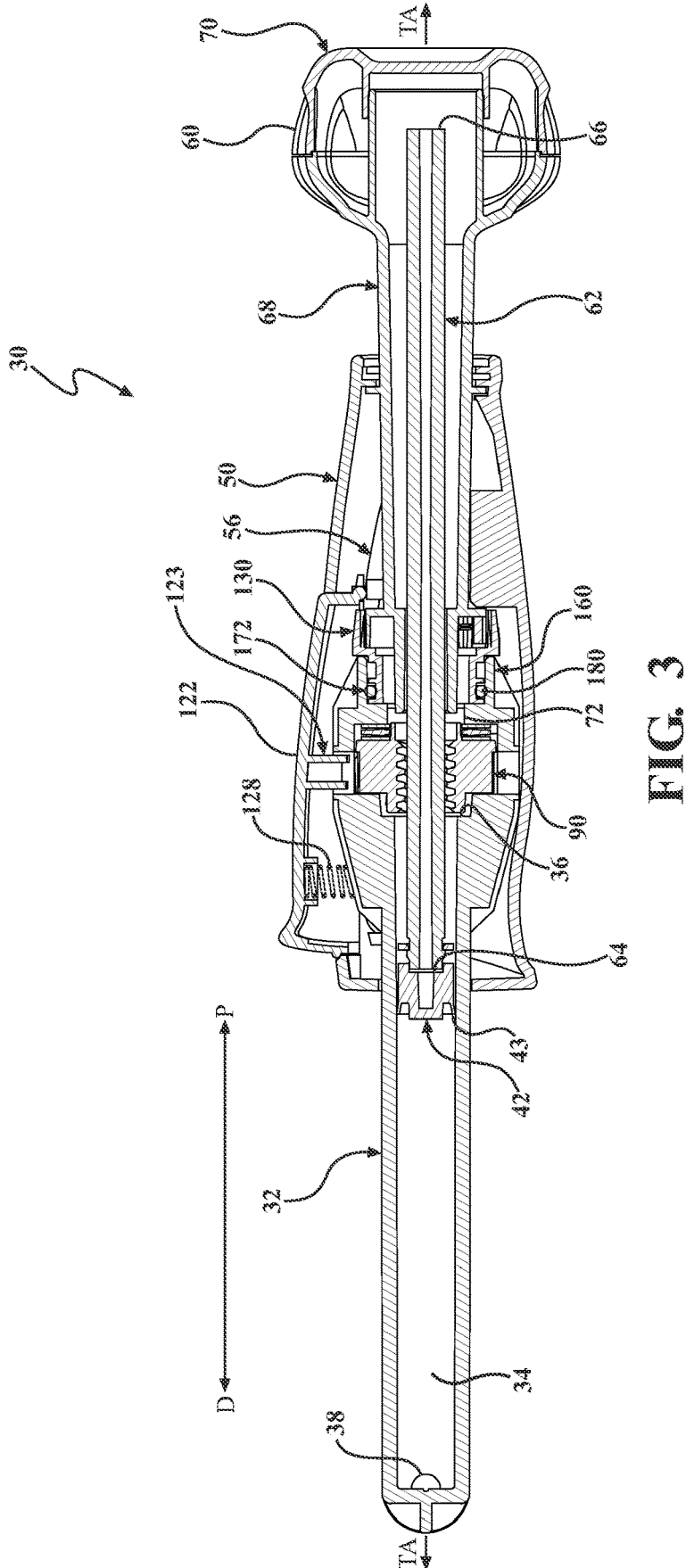
FIG. 3 is a sectional view of the curable material dispensing system of FIG. 2 taken along section lines 3-3. An actuator is in a disengaged position.
Figures 4, 5:
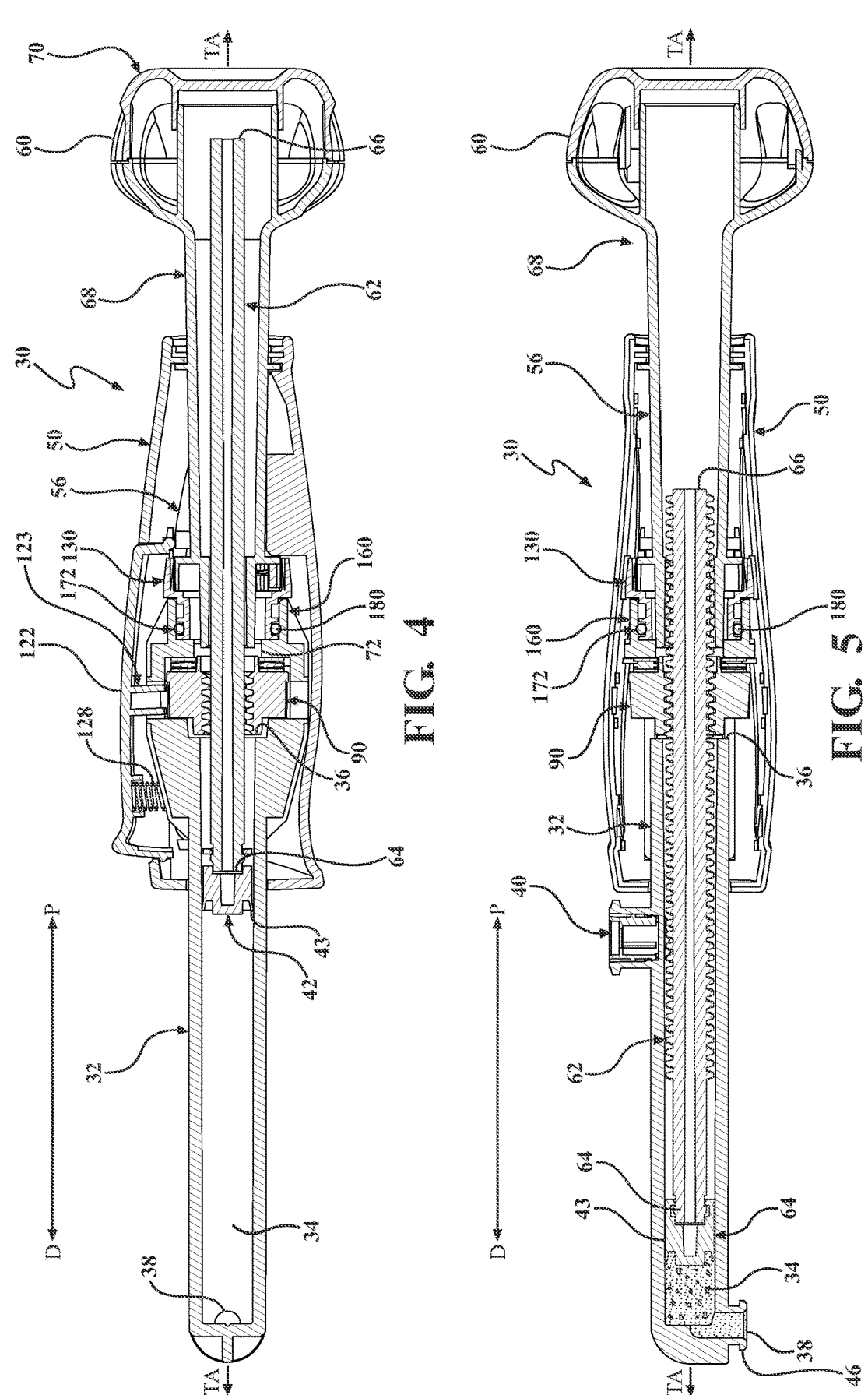
FIG. 4 is a sectional view of the curable material dispensing system with the actuator in an engaged position.
FIG. 5 is a sectional view of the curable material dispending system with a lead screw advanced distally to compress and/or dispense curable material.

Referring to FIG. 5, the plunger 42 is slidably disposed within the dispensing volume 34. The plunger 42 is movable within the dispensing volume 34 in a distal direction (D) and a proximal direction (P). In particular, the plunger 42 is adapted to be advanced in the distal direction, to urge and/or compress the curable material (CM) within the dispensing volume 34, thereby urging at least a portion of the compressed curable material from the distal outlet 38. To facilitate the distal advancement of the plunger 42, the curable material dispensing system 30 includes a first control surface 60 adapted to receive a primary input from a user, and a lead screw 62 operably coupled to the first control surface 60. The plunger 42 is coupled to the lead screw 62, for example, at or near a distal end 64 of the lead screw 62, as shown in FIGS. 3 and 5. The lead screw 62 may be rotatably fixed relative to the first control surface 60. In a manner to be further described, the application of the primary input force, for example, a first torque input to the first control surface 60 in a first direction provides for rotation of the lead screw 62 with corresponding distal advancement of the plunger 42 within the dispensing volume 34. Conversely, the application of a second torque input to the first control surface 60 in a second direction opposite the first direction may provide for rotation of the lead screw 62 with corresponding movement of the plunger 42 in the proximal direction within the dispensing volume 34. It is contemplated that the plunger 42 may be rotatable relative to the lead screw 62 in a manner to reduce friction between the plunger 42 and the lead screw 62. The reduced friction between the plunger 42 and the lead screw 62 may facilitate backdriving of the system 30, such as during the movement of the plunger 42 in the proximal direction.

Figure 8:
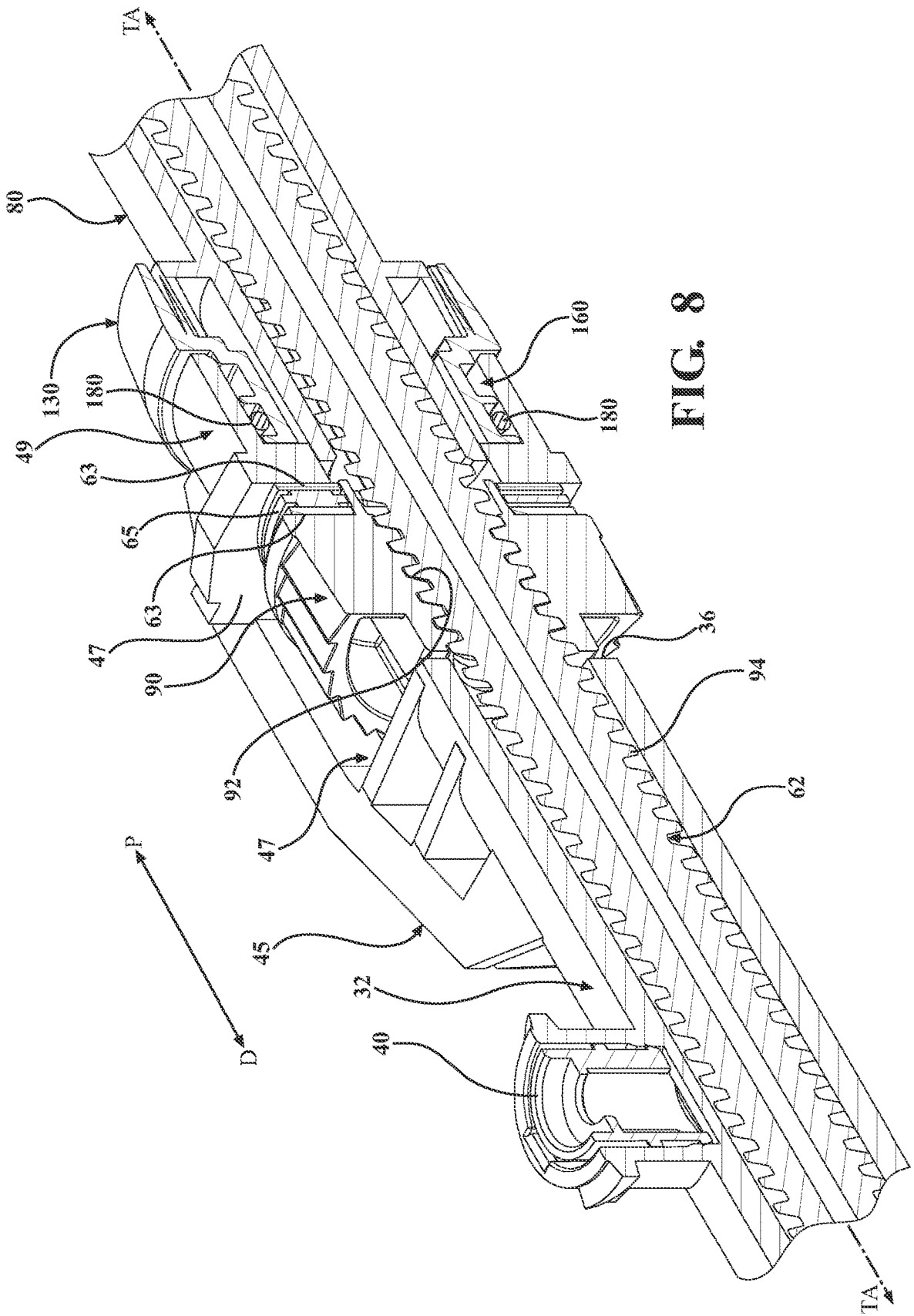
FIG. 8 is a perspective sectional view of the curable material dispensing system of FIG. 7 taken along section lines 8-8.
Figure 9:
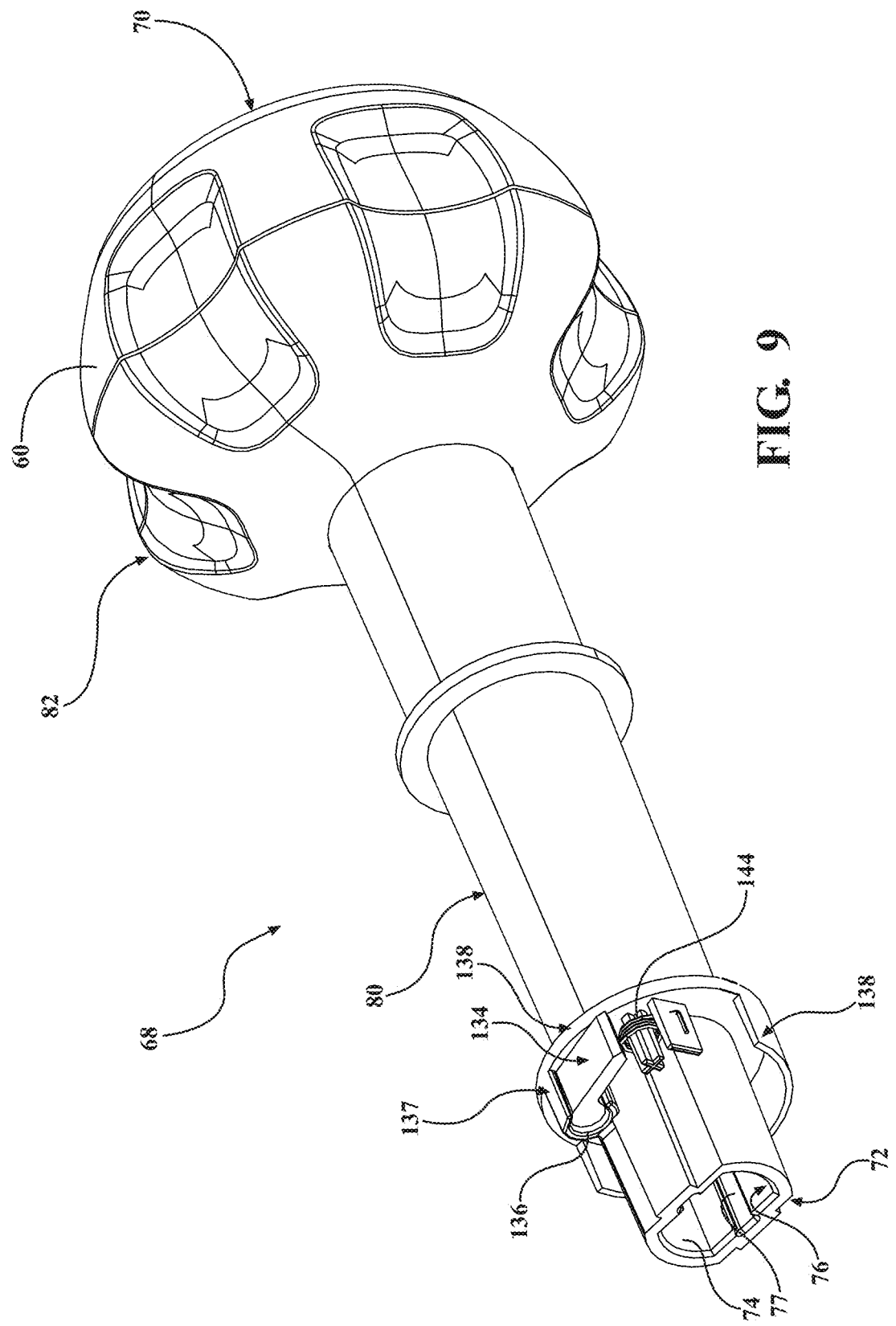
FIG. 9 is a perspective view of a handle defining a first control surface and including features of a unidirectional torque mechanism.

Referring now to FIGS. 3-5 and 8, the lead screw 62 includes the distal end 64 and a proximal end 66 opposite the distal end 64. A translation axis (TA) may be defined between the proximal and distal ends 64, 66 of the lead screw 62. The first control surface 60 may be associated with a handle 68. The handle 68 may include a proximal end 70, a distal end 72, and a lumen 74 at least partially extending between the proximal and distal ends 70, 72 of the handle 68. The lumen 74 may be coaxially disposed on the translation axis with at least a portion of the handle 68 extending from the interior 56 of the housing 50. The proximal end 66 of the lead screw 62 may be positioned within the lumen 74, as best shown in FIGS. 3-5. The handle 68 may further include drive features 76 defining at least a portion of the lumen 74. The drive features 76 of the handle 68 are adapted to engage with driven features 78 of the lead screw 62 complimentary to the drive features 76 such that the lead screw 62 is rotatably fixed relative to the first control surface 60 of the handle 68. With reference to FIG. 9, for example, the drive features 76 may define a rectangular-shaped lumen at least partially extending between the proximal and distal ends 70, 72 of the handle 68. The drive features 76 may further include slots 77 at least partially defining the lumen 74. The driven features 78 may be defined by the proximal end 66 of the lead screw 62 being at least substantially rectangular and sized to the lumen 74 of the handle 68. The driven features 78 may further include at least one ridge 79 (e.g., defined by a chord of the lead screw 62) extending longitudinally along the lead screw 62. The drive and driven features 76, 78 are engaged to prevent relative rotation between the lead screw 62 and the handle 68, but permit axial movement of the lead screw 62 relative to the first control surface 60 of the handle 68 along the translation axis.

The handle 68 may include a shaft 80 and a grip portion 82 coupled to the shaft 80. The grip portion 82 at least partially defines the first control surface 60. FIG. 8 shows the grip portion 82 positioned proximal to and extending radially outwardly from the shaft 80. The grip portion 82 is sized to be griped by one hand of the physician during operation. The first control surface 60 may be annularly disposed about the grip portion 82. At least the first control surface 60 of the grip portion 82 may be formed from material(s) with increased tack (e.g., rubber) to prevent inadvertent slipping of the hand during application of the first and second torque inputs to the first control surface 60. Further, at least the first control surface 60 of the grip portion 82 may include indentations and/or ridges to facilitate improved grip during use. Directional indicia (not shown) may be disposed on the handle 68 to provide guidance to the physician as to the first direction of rotation.

Figure 7:
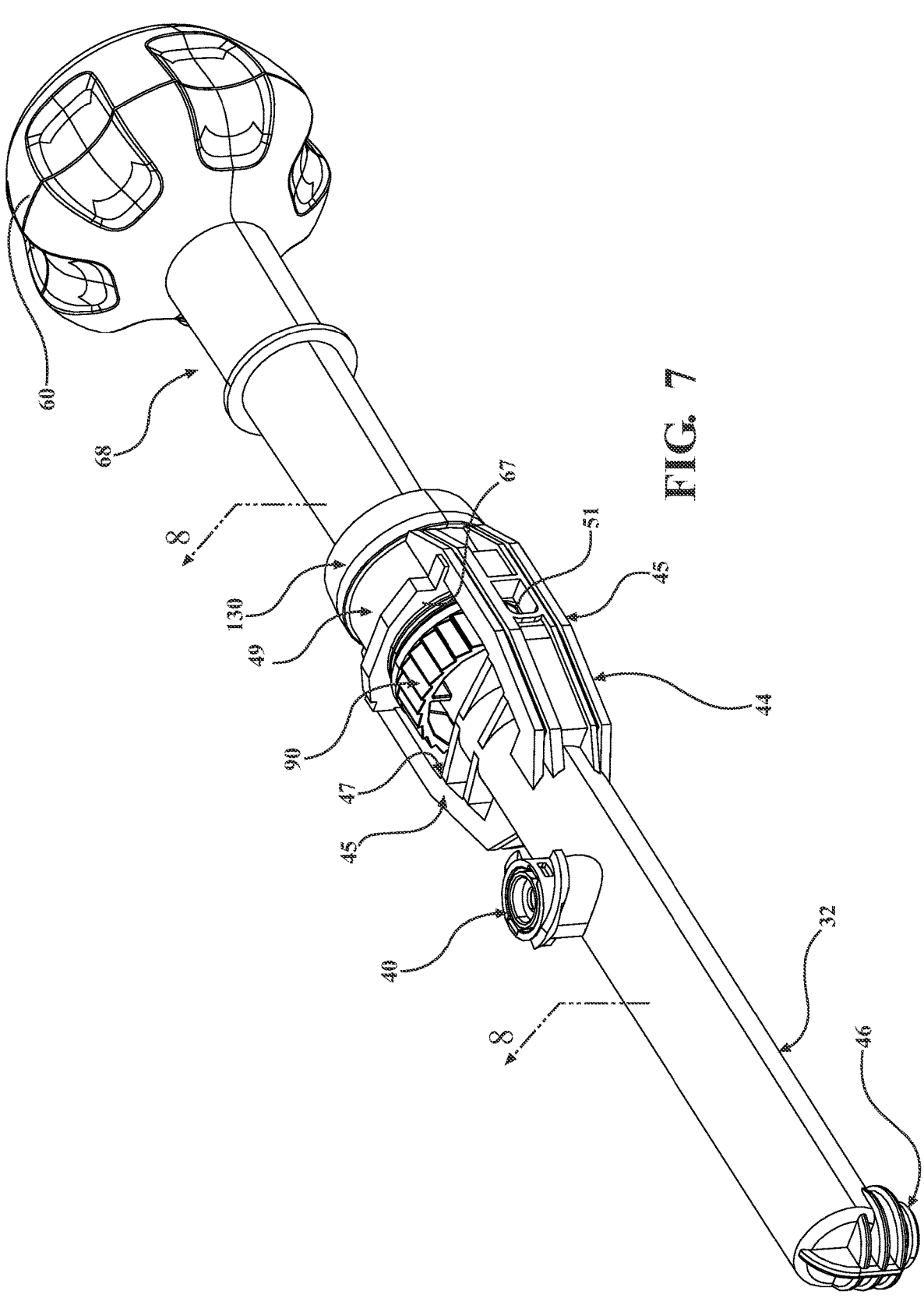
FIG. 7 is a perspective view of the curable material dispensing system with the actuator and housing removed.

When the lead screw 62 is rotatably fixed relative to the first control surface 60, providing the first and second torque inputs to the first control surface 60 imparts rotation of the handle 68 and therefore, rotation of the lead screw 62. Yet the distal and proximal movement of the plunger 42 along the translation axis requires corresponding distal and proximal movement of the lead screw 62 coupled to the plunger 42. To facilitate, for example, distal movement of the plunger 42 and the lead screw 62 along the translation axis, the curable material dispensing system 30 includes a locking nut 90 including internal threads 92. With particular reference to FIGS. 8 and 8, the internal threads 92 of the locking nut 90 threadably engage external threads 94 of the lead screw 62 at least partially extending between its proximal and distal ends 64, 66. The locking nut 90 may be disposed within the interior 56 of the housing 50 and disposed coaxially on the translation axis. The locking nut 90 includes an aperture 96 for receiving the lead screw 62. FIG. 7 shows the lead screw 62 coaxially extending through the aperture 96 of the locking nut 90 with the internal threads 92 of the locking nut 90 in threadable engagement with the external threads 94 of the lead screw 62. The threadable engagement of the internal threads 92 of the locking nut 90 and the external threads 94 of the lead screw 62 provides for the distal advancement of the lead screw 62 (and the plunger 42) relative to the locking nut 90 in response to the first control surface 60 receiving the first torque input from the user. It is noted that the internal threads 92 of the locking nut 90 extend about an entirety of the aperture 96 (i.e., 360 degrees), whereas the external threads 94 encircle less than an entirety of the lead screw 62 to define partial threading (e.g., 90, 180, 270 degrees, etc.). The ridge(s) 79 extend between portions of the lead screw 62 not having the external threads 94. Alternatively, the internal threads 92 and/or the external threads 94 may extend about and encircle, respectively, all or less than 360 degrees.

Figure 10:
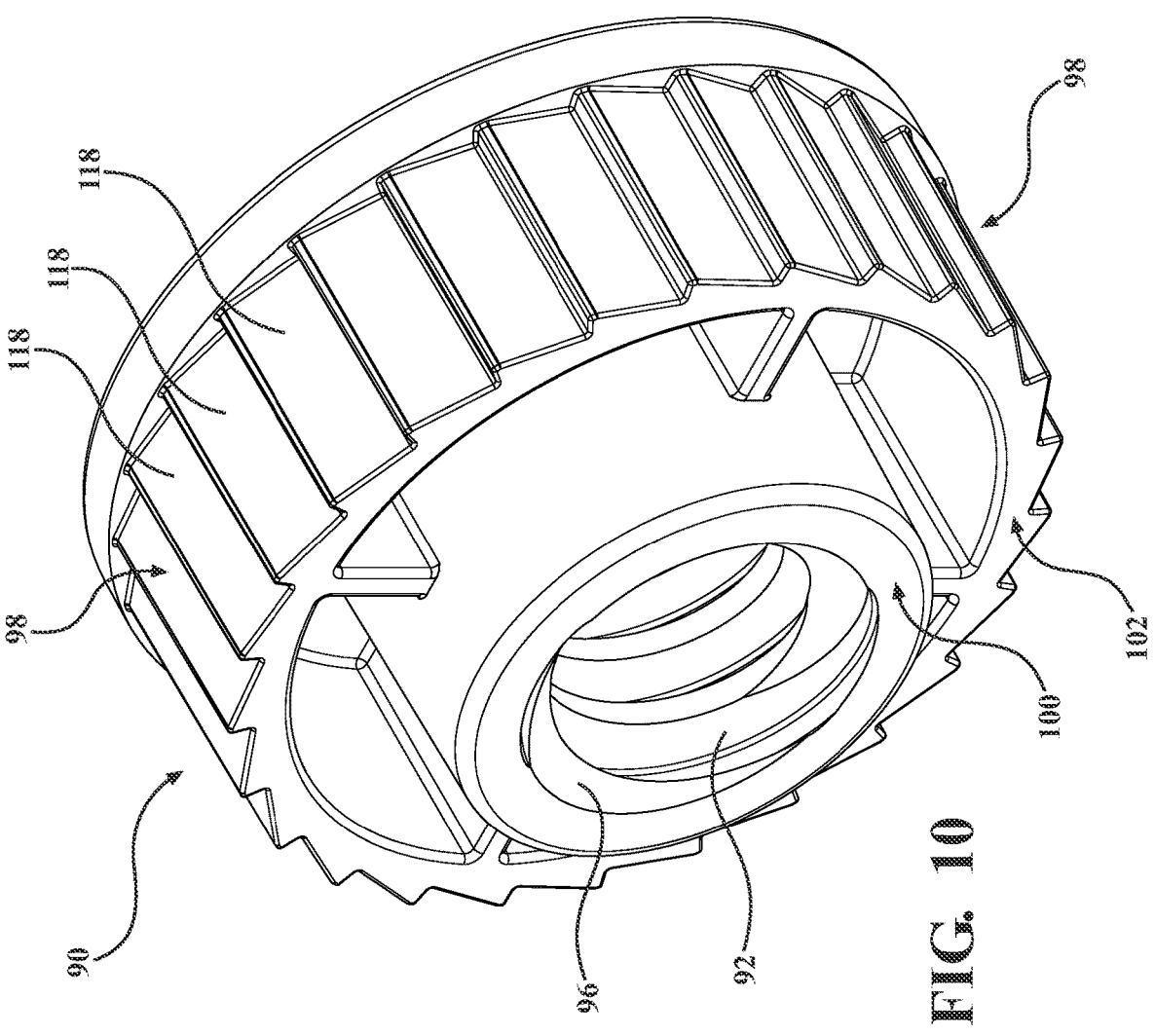
FIG. 10 is a front perspective view of the locking nut.
Figure 11:
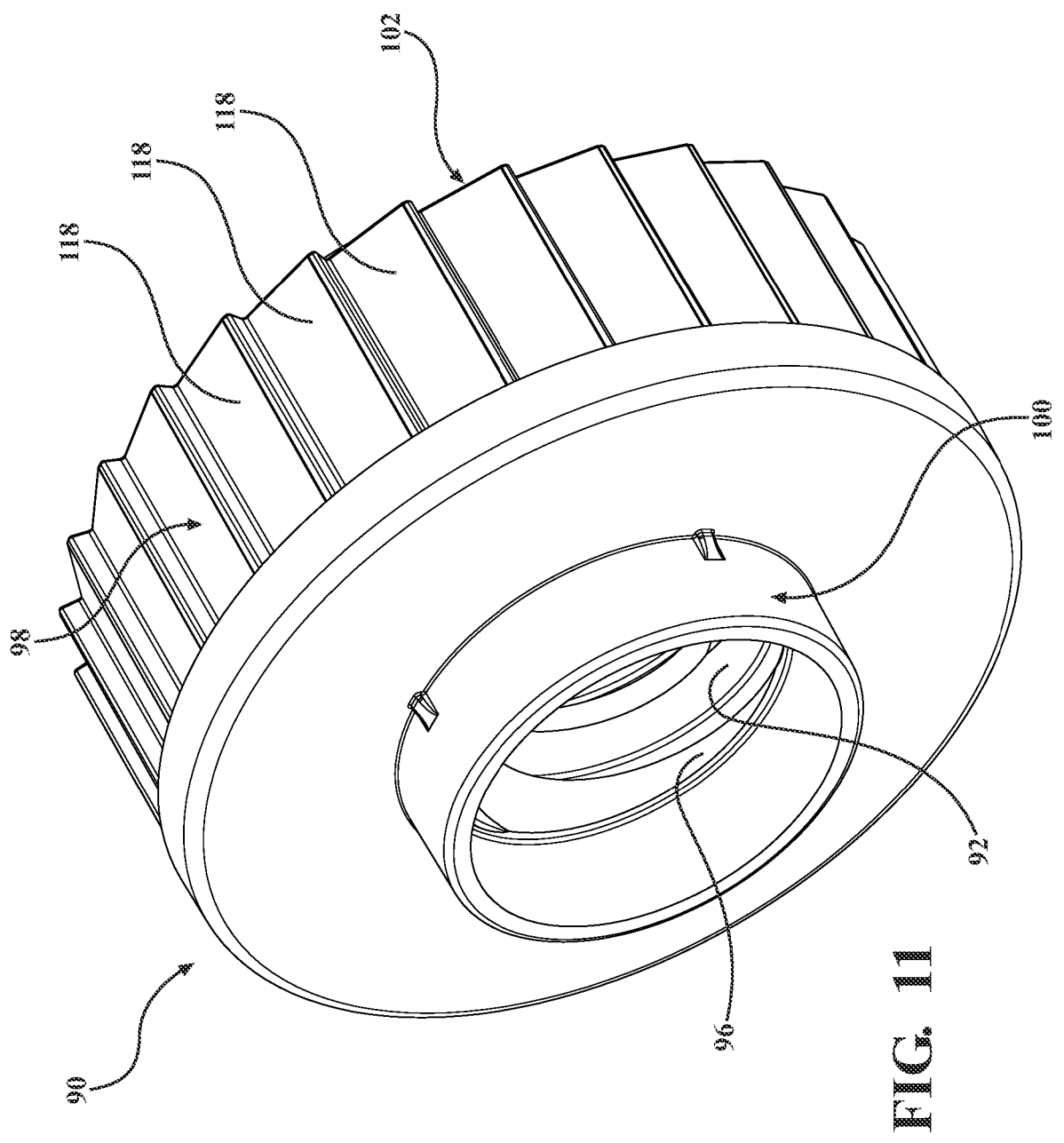
FIG. 11 is a rear perspective view of the locking nut.
Figure 13:
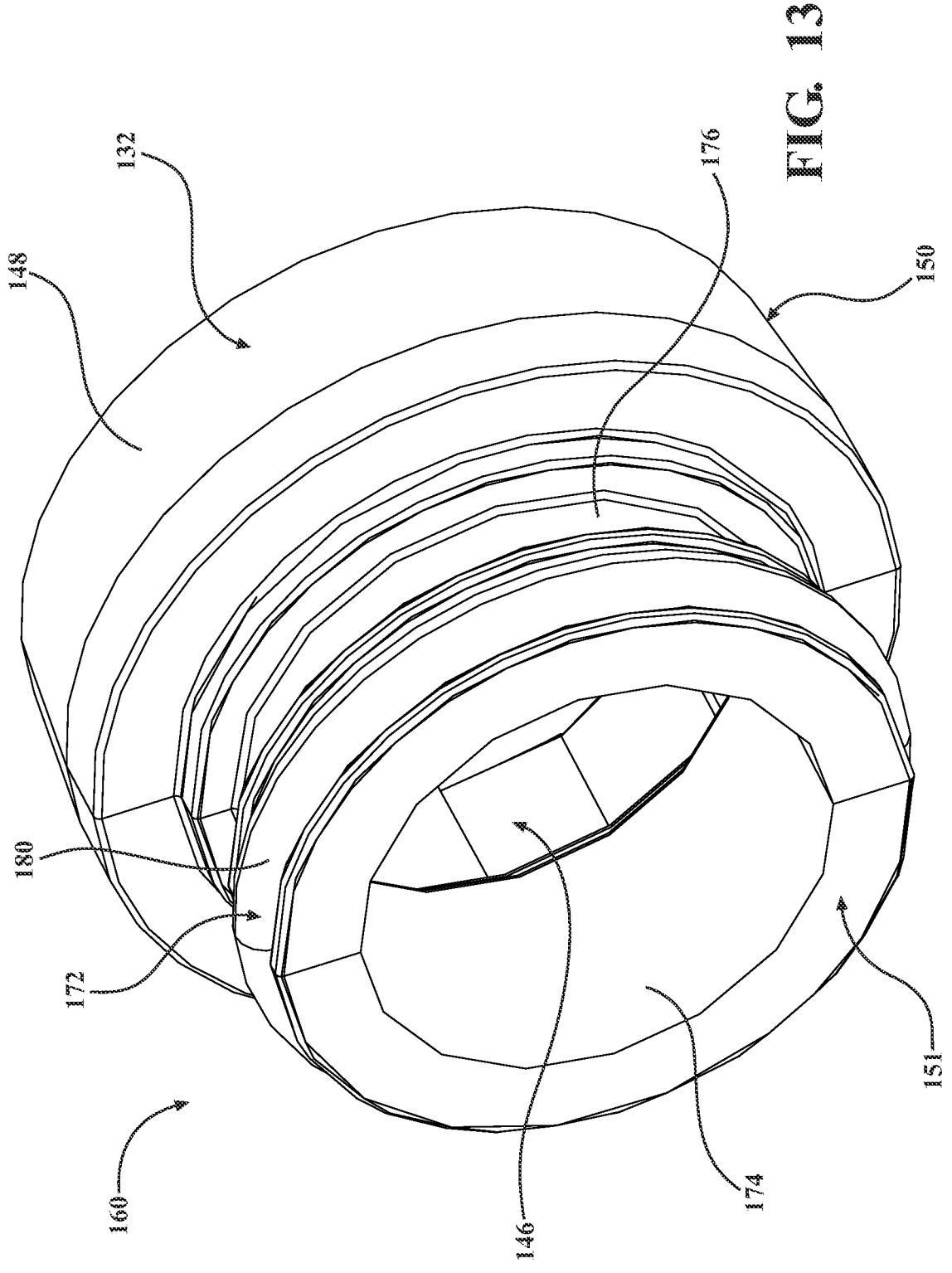
FIG. 13 is a front perspective view of a defeatable unidirectional mechanism.

FIGS. 8, 10 and 13 best show the locking nut 90 including a hub 100 and a ring gear 102 coupled to the hub 100. The hub 100 defines the aperture 96 and includes the internal threads 92 disposed about the aperture 96. The hub 100 may be disposed within a recess defined by the ring gear 102. The aperture 96 may be defined by the hub 100 and sized to receive the lead screw 62. The locking nut 90 may be formed from suitable materials including polymers, metals, combinations thereof, and the like.

The curable material dispensing system 30 provides for selectively preventing rotation of the locking nut 90 about the translation axis, resulting in the locking nut 90 providing for the distal advancement of the lead screw 62 with rotation of the same. Otherwise, when the locking nut 90 is permitted to rotate about the translation axis, rotation of the lead screw 62 results in concurrent rotation of the lead screw 62 and the locking nut 90 (due to characteristics of the internal threads 92 and the external threads 94) with minimal distance advancement of the lead screw 62 relative to the locking nut 90. Yet when the locking nut 90 is prevented from rotation about the translation axis, rotation of the lead screw 62 results in the distal advancement of the lead screw 62 relative to the locking nut 90 due to the threadable engagement between the internal threads 92 of the locking nut 90 and the external threads 94 of the lead screw 62. Likewise, when the locking nut 90 is prevented from rotation relative to the housing 50, rotation of the lead screw 62 results in the distal advancement of the lead screw 62 relative to the housing 50 due to the threadable engagement between the internal threads 92 of the locking nut 90 and the external threads 94 of the lead screw 62.

In order to selectively prevent rotation of the locking nut 90 about the translation axis, the locking nut 90 may include an engagement feature 98. In a manner to be described, the engagement feature 98 is adapted to be engaged (with application of a secondary input force) to prevent rotation of the locking nut 90 about the translation axis. The engagement feature 98 may include a plurality of teeth 118. The teeth 118 may extend radially from the ring gear 102, and more particularly, be disposed annularly about the ring gear 102 of the locking nut 90. The teeth 118 may be disposed about the distal and/or proximal rings 104, 105 forming the ring gear 112 of the locking nut 90. Alternatively, the engagement feature may be a notch, protrusion, etc.

Returning again to FIGS. 3 and 4, the system 30 may include an actuator 120 adapted to selectively engage the engagement feature 98 of the locking nut 90. The actuator 120 includes a second control surface 122 adapted to receive the secondary input force from the user. The actuator 120 further includes an engagement feature 123 complimentary to the engagement feature 98 of the locking nut 90, for example, complimentary teeth 124. With concurrent reference to FIG. 14, the actuator 120 may be a lever 126 pivotably coupled to the housing 50. The illustrated lever 126 is generally rectangular in shape and defines the second control surface 122 oriented away from the housing 50 so as to receive the secondary input force from the user. Alternatively, the actuator 120 may be a button, toggle switch, slider, and the like.

The teeth 124 are coupled to the actuator 120 and positioned generally opposite to the second control surface 122 so as to be oriented towards the locking nut 90. The teeth 124 may be arranged in a manner complimentary to an arcuate portion of the teeth 118 extending annularly about the locking nut 90. It is further contemplated that the actuator may be movable coupled to the housing 50 in other ways beyond pivotable coupling, such as slidable engagement, etc. The actuator 120 is operable between an engaged position and a disengaged position. In the engaged position, the complimentary engagement feature 123 engages the engagement feature 98 of the locking nut 90 to prevent rotation of the locking nut 90 about the translation axis. For example, the teeth 124 of the actuator 120 engage the teeth 118 of the locking nut 90. With the actuator 120 coupled to the housing 50, the locking nut 90 is rotatably fixed relative to the housing 50 when the actuator 120 is in the engaged position. In the disengaged position, the teeth 124 of the actuator 120 are spaced away from or otherwise disengaged from the teeth 118 of the locking nut 90. The locking nut 90 may rotate about the translation axis and relative to the housing 50 when the actuator 120 is in the disengaged position. The secondary input force provided to the second control surface 122 moves the actuator 120 between the engaged and disengaged positions. For example, the lever 126 may be initially in the disengaged position represented in FIG. 3. The user applies the secondary input force, such as a downward force to the lever 126 while supporting the housing 50. The lever 126 pivots relative to the housing 50 with the teeth 124 of the actuator 120 moving towards the teeth 118 of the locking nut 90. The teeth 118, 124 mesh to further define the engaged position of the actuator 120.

The system 30 may include a biasing member 128 operably coupled to the actuator 120. The biasing member 128 may bias the actuator 120 towards the disengaged position. For example, FIG. 3 shows the biasing member 128 being a coil spring adapted to engage a recess 129 on an underside of the actuator 120 (see FIG. 9). When the actuator 120 is in the engaged position, as shown in FIG. 4, the coil spring is compressed between the actuator 120 and the housing 50. Thus, the biasing member 128 may be adapted to bias the lever 126 away from the housing 50. As a result, application of the secondary input force to the second control surface 122 overcomes a biasing force provided by the biasing member 128 to move the actuator 120 from the disengaged position to the engaged position. Conversely, removal of secondary input force from the second control surface 122 provides for the biasing member 128 moving the actuator 120 from the engaged position to the disengaged position. The biasing member 128 may alternatively be a torsion spring, spring clip, constant force spring, or other suitable mechanism for biasing the actuator 120 to the disengaged position.

Alternatively, it is contemplated that the biasing member may be coupled to the in a manner that biases the actuator 120 to the engaged position, and the secondary input force applied to the second control surface 122 moves the actuator 120 from the engaged position to the disengaged position (i.e., the converse arrangement than as previously described). In such an implementation, the engagement feature 98 of the locking nut 90 may be engaged with, for example, teeth (not shown) positioned opposite the locking nut 90 from the actuator 120. The teeth are biased into engagement with the engagement feature 98 in the absence of the input of the secondary input force to the second control surface 122. The actuator 120 is biased into a position away from the locking nut 90 (e.g., the position shown in FIG. 2). Further, the actuator 120 is operably coupled to the teeth positioned opposite the locking nut 90. The application of the secondary input force to the second control surface 122 moves the actuator 120 towards the housing 50, which disengages the teeth from the engagement feature 98 against the biasing force provided by the biasing member. The locking nut 90, no longer constrained by the teeth rotatably fixed relative to the housing 50, may then rotate about the translational axis for reasons described throughout the present disclosure.

With the actuator 120 in the engaged position, application of the primary input force to the first control surface 60 results in rotation of the lead screw 62 about the translation axis and distal advancement along the translation axis due to the threadable engagement between the lead screw 62 and the locking nut 90. The distal advancement of the lead screw 62 results in the distal advancement of the plunger 42 within the dispensing volume 34. The curable material within the dispensing volume 34 is compressed and/or dispensed from the distal outlet 38. In the context of an exemplary surgical procedure for use with the curable material dispensing system 30, namely a vertebroplasty, the curable material may be dispensed to the extension tube 190 and through the access cannula directed through the cortical bone and into the cancellous region of the vertebral body.

Yet for any number of reasons, it may be desirable for the physician to immediately cease delivery of the curable material into, for example, the cancellous region of the vertebral body. As mentioned, one example is recognition an excessive amount of the curable material being introduced into the body. Despite removal of the physician's input, many known systems result in "drool" and additional curable material being delivered into the patient, contrary to the intentions of the physician. One of the many advantageous features of the system 30 of the present disclosure includes providing for proximal movement of the lead screw 62 (and the plunger 42) in a manner that minimizes or eliminates drool from the distal outlet 38 of the dispensing volume 34. In a manner to be explained in greater detail, the internal threads 92 of the locking nut 90 and the external threads 94 of the lead screw 62 are configured to provide for rotation of the locking nut 90 about the translation axis when the actuator 120 is in the disengaged position. The rotation of the locking nut 90 permits the plunger 42 to move proximally along the translation axis, and further permit the compressed curable material to at least partially decompress within the dispensing volume 34, as opposed to decompressing through the distal outlet 38.

Returning to FIG. 4, the system 30 is shown with the actuator 120 in the engaged position. In particular, the lever 126 may be positioned adjacent the housing 50 with the second control surface 122 substantially flush with the housing 50. The teeth 124 of the actuator 120 engage the teeth 118 of the locking nut 90 such that the locking nut 90 is rotatably fixed relative to the housing 50. As previously described, application of the first torque input to the first control surface 60 results in rotation of the lead screw 62 relative to the locking nut 90, which further provides for advancement of the lead screw 62 in the distal direction (D) along the translation axis (TA). The distal advancement of the lead screw 62 results in advancement of the plunger 42 in the distal direction and corresponding compression of the curable material (CM) within the dispensing volume 34 (see FIG. 5). In certain operating conditions, the curable material may be compressed to 200, 500, 1000, 3000, or 5000 or more pounds per square inch (psi). The compression of the curable material results in forces on the plunger 42 along the translation axis in the proximal direction (P).

Should the physician desire to immediately cease delivery of the curable material from the dispensing volume 34, the secondary input force provided to the second control surface 122 is simply removed. In manners previously described, the biasing member 128 biases the actuator 120 away from the housing 50 and from the engaged position to the disengaged position. Upon release of the secondary input force, the teeth 124 of the actuator 120 automatically disengage from the teeth 118 of the engagement feature 98 of the locking nut 90. The locking nut 90, no longer constrained by the actuator 120 rotatably fixed relative to the housing 50, may rotate about the translation axis.

The rotation of the locking nut 90 about the translation axis permits the lead screw 62 to move in the proximal direction along the translation axis. The lead screw 62 is urged in the proximal direction along the translation axis by the forces on the plunger 42 from the curable material compressed within the dispensing volume 34. The lead screw 62 translates in the proximal direction without rotation as the locking nut 90 rotates about the translation axis without translation. It is contemplated that some translation of the locking nut 90 may be provided or occur. The translation of the lead screw 62 in the proximal direction results in an increase in the dispensing volume 34 accessible to the compressed curable material. In other words, a portion of the dispensing volume 34 defined within the chamber 32 distal to the plunger 42 is increased. The curable material at least partially decompresses within the increased portion of the dispensing volume 34 now accessible to the compressed curable material. Further, with a diameter of the chamber 32 often being greater than a diameter of the distal outlet 38, even minimal movement of the plunger 42 in the proximal direction provides increased volume within the dispensing volume 34 for the curable material to decompress. In other words, the compressed curable material encounters less resistance within the increased portion of the dispensing volume 34 as opposed to exiting the distal outlet 38. The curable material is decompressed sufficiently to reduce the pressure gradient between the dispensing volume 34 and the surgical site in view of the viscosity of the partially compressed curable material. Therefore, the likelihood of drool is minimized or eliminated with the curable material dispensing system 30.

The movement of the lead screw 62 in the proximal direction is based on the interaction between the internal threads 92 of the locking nut 90 and the external threads 94 of lead screw 62. In other words, the internal threads 92 of the locking nut 90 and the external threads 94 of lead screw 62 are configured to provide for a backdrivable system. The backdrivable system may include the internal threads 92 of the locking nut 90 and the external threads 94 of lead screw 62 being defined by a screw efficiency of greater than 50%. In other words, if the screw efficiency is less than 50%, based on, for example, pitch of the threads 92, 94, friction between the threads 92, 94, and the like, the system 30 will not be backdrivable and the locking nut 90 will not rotate in response to the torque being transferred from the lead screw 62 being urged proximally by the compressed curable material. Stated differently, the forces from the compressed curable material on the plunger 42 and the lead screw 62 in the proximal direction results in a torque on the locking nut 90 greater than a backdriving torque ($T_b$) of the system 30 according to Equation 1:

$$T_b = \frac{(F * P * n_2)}{2\pi},$$ (1)

where F is the axial load, P is the screw lead, and 112 is the efficiency of the screw. Consequently, if the backdriving torque ($T_b$) of the system 30 is greater than the total friction torque, backdriving will occur. It is contemplated that any suitable material and dimensional design characteristics may be provided to the lead screw 62 and/or the locking nut 90 in order to achieve screw efficiency of greater than 50% and provide for translation of the lead screw 62 along the translation axis with corresponding rotation of the locking nut 90 about the translation axis. For example, having the external threads 94 not fully encircle the lead screw 62 may facilitate achieving lesser friction and greater screw efficiency.

In addition to minimizing or eliminating drool, the design of the lead screw 62 of the system 30, including the screw efficiency, provides for several additional benefits to be described. First, the forces from the compressed curable material on the plunger 42 (e.g., backpressure) is more efficiently transmitted to the hand(s) of the physician holding the system 30, and in particular the first control surface 60. This improves tactile feel for the physician, which may further provide for improved awareness of the volume of the curable material being dispensed from the dispensing volume 34 during use of the system 30. In other words, frictional losses within the system 30 are minimized, and thus more precise control is realized with each first torque input to the first control surface 60 resulting in predictable and precise volumes being dispensed from the dispensing volume 34. Second, efficiency is not sacrificed with the improved tactile feel provided to the physician. The mechanical advantage of the system 30 is substantially preserved, which among other things, limits physician fatigue and avoids loss of procedure operating time often hampering less robust systems. Third, the preserved mechanical advantage of the system 30 also results in the compressed curable material being rapidly delivered to the patient per torque input of the physician (i.e., a "fast start"). In other words, the lead screw 62 requires less turns to dispense the same amount of curable material to the patient relative to known systems with appreciable frictional losses. In one example, approximately 0.8 to 1.0 cubic cementers of curable material may be delivered per 360° revolution of the first control surface 60 without significant loss in mechanical advantage. Known systems with lead screws are limited to less than 0.5 cubic cementers per 360° revolution; otherwise, the frictional losses associated with a higher pitched lead screws require undesirably high inputs from the physician with associated increase in fatigue and working time. It is further contemplated that the internal threads 92 of the locking nut 90 and the external threads 94 of lead screw 62 may be modified as desired to alter the characteristics of the fast start. Likewise, lubricants and/or coatings may be applied to the lead screw 62 and/or the locking nut 90 to alter the characteristics of the fast start.

Figure 6:
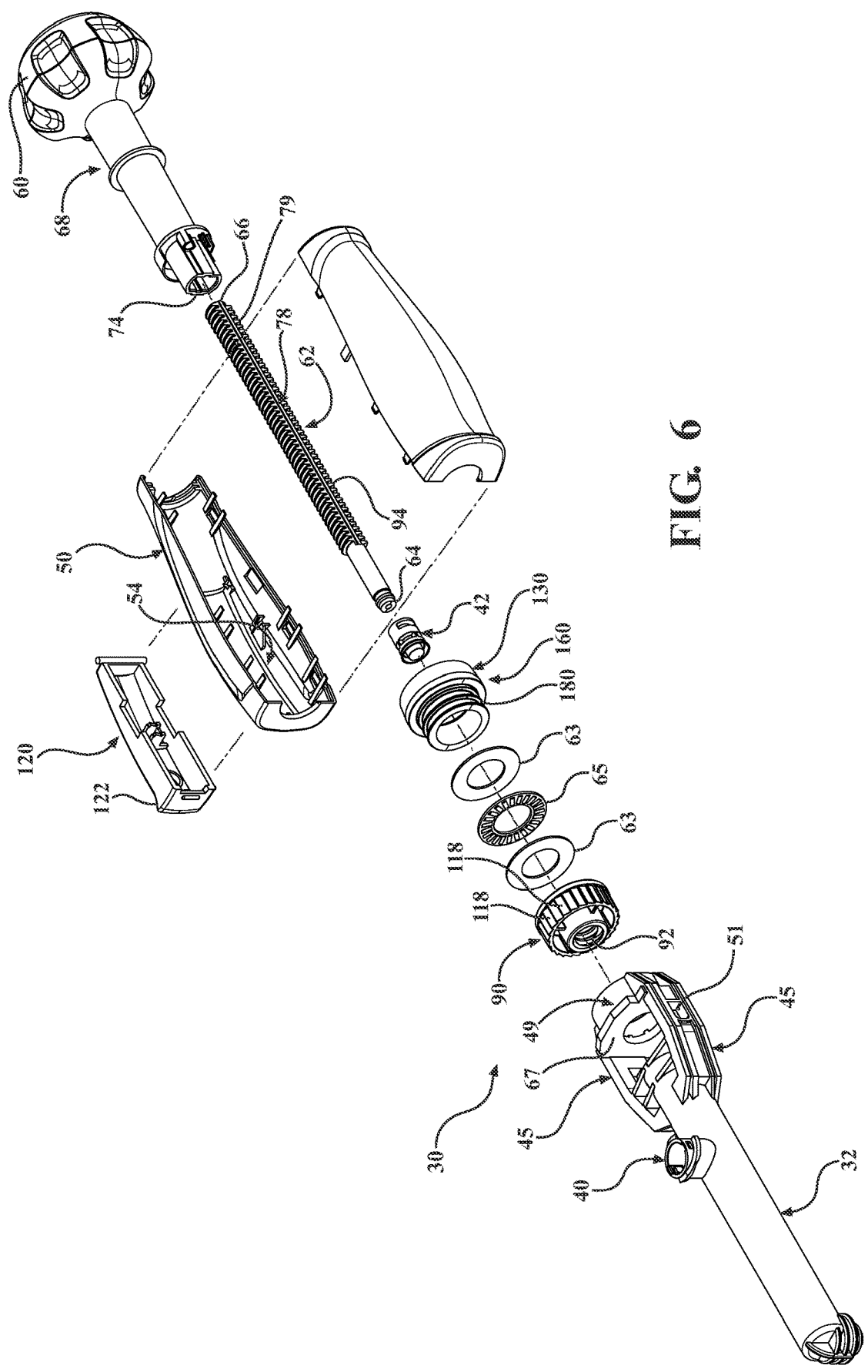
FIG. 6 is an exploded view of the curable material dispensing system.

When the plunger 42 and the lead screw 62 are moving in the proximal direction, in particular during the backdriving of the system 30, it is desirable to limit or eliminate translation of the locking nut 90 along the translation axis. In particular, limiting or eliminating translation of the locking nut 90 along the translation axis more efficiently provides for rotation of the locking nut 90 about the translation axis for reasons previously described. Therefore, it is contemplated to include one or more bushings 63 and/or one or more bearings 65 positioned adjacent to or in abutment with the locking nut 90 within the interior 56 of the housing 50. FIGS. 6 and 8 shows the system 30 including two bushings 63 with the bearing 65 being a thrust bearing positioned intermediate the two bushings 63. Suitable means for reducing friction other than the thrust bearing are contemplated, such as ball bearings, needle bearings, lubricants, coatings, and the like. The tolerances between the bushings 63, the bearing 65, and the proximal ring 49 are designed to minimize or eliminate translation of the locking nut 90 in the proximal direction along the translation axis, and the bearing 65 is configured to facilitate rotation of the locking nut 90 about the translation axis.

As the plunger 42 is urged in the proximal direction along the translation axis by the forces on the plunger 42 from the curable material compressed within the dispensing volume 34, the axial forces are transmitted to the lead screw 62 and the locking nut 90 in threadable engagement with the lead screw 62. At least portion of the chamber mount 44, in particular the proximal ring 49, may define a loadbearing surface 67, is adapted to accommodate stress, strain, fatigue, wear, and the like, associated with appreciable forces transmitted from the compressed curable material to the lead screw 62 and the locking nut 90. In particular, the chamber mount 44 may define the void 47 sized to receive the locking nut 90, the bushing(s) 63, and/or the bearing 65. The axial forces may be transmitted from the locking nut 90, the bushings 63, and the bearing 65, to the loadbearing surface 67 and the opposing struts 45 fixed to the chamber 32. In such an implementation, the housing 50 may be considered non-loadbearing, and thus may be formed from less robust materials and/or less complex manufacturing processes. In particular, the void 47 accommodating the locking nut 90 is effectively integral into the chamber 32 (via the opposing struts 45) such that, when the chamber 32 is coupled to the housing 50, forces transmitted from the compressed curable material to the lead screw 62 and the locking nut 90 are internalized or dissipated within the chamber 32 itself.

Other suitable designs of the chamber 32, the chamber mount 44, and/or the housing 50 are contemplated consistent with the objects of the above disclosure. In one example, the second control surface 122 is operably coupled to the chamber 32 (as opposed to the housing 50) with the engagement features 98 coupled to the second control surface 122 configured to engage the teeth 118 of the locking nut 90 manners previously described. In such an example, any loading on the second control surface 122 (e.g., at the pivot of the lever 126) is internalized or dissipated within the chamber 32 itself, further rendering the housing 50 non-loadbearing.

As previously described in detail, the curable material dispensing system 30 provides for distal advancement of the plunger 42 in response to the first control surface 60 receiving the primary input force (e.g., the first torque input to the handle 68) with the actuator 120 in the engaged position. This may be effectuated by the physician applying the secondary input force to the second control surface 122 to maintain the actuator 120 in the engaged position with one hand, while simultaneously applying the first torque input to the first control surface 60 with another hand. For any number of reasons, the physician may remove the first hand from the first control surface 60. Most often, the physician does so in order to reset his or her hand for a subsequent application of the first torque input. Another example may include the physician needing to perform another aspect of the surgical procedure with the first hand while supporting the system 30 with the second hand. Yet based on the backdrivable aspects of the lead screw 62 and the locking nut 90, removing the primary input force from the first control surface 60 (with the actuator 120 in the engaged position) would otherwise result in the compressed curable material within the dispensing volume 34 forcing the plunger 42 and the lead screw 62 to rotate (and move in the proximal direction) with corresponding rotation of the first control surface 60. In other words, with the actuator 120 in the engaged position, the threads 92, 94 would cause the lead screw 62 to rotate within the locking nut 90 rotatably fixed relative to the housing 50. The rotation of the lead screw 62 in the second direction would sacrifice the distal advancement of the plunger 42, and undesirably require the physician to reestablish the position of the plunger 42 before continuing with the procedure. To overcome this potential shortcoming, the curable material dispensing system 30 includes the unidirectional torque mechanism 130.

Referring now to FIGS. 2-5, 9, 14 and 15, the unidirectional torque mechanism 130 may be operably coupled to the first control surface 60. The unidirectional torque mechanism 130 may be adapted to permit for rotation of the first control surface 60 about the translation axis in the first direction (e.g., $R_1$ of FIG. 2), and generally prevent rotation of the first control surface 60 about the translation axis in the second direction (e.g., $R_2$ of FIG. 2). More specifically, the unidirectional torque mechanism 130 permits the distal advancement of the lead screw 62 during application of the first torque input to the handle 68 in the first direction, and prevent proximal movement of the lead screw 62 upon removal of the first torque input. As a result, the physician is free to rotate the handle 68 in the first direction to distally advance the plunger 42 by a desired extent, then reset his or her hand on the handle 68 and/or perform another aspect of the surgical procedure without sacrificing the distal advancement of the plunger 42.

The unidirectional torque mechanism 130 may be a ratcheting mechanism including a ratchet member such as a ratchet ring 132 and at least one pawl 134. The pawl 134 is seated within a recess 136 defined by a flange 137 coupled to the handle 68. FIG. 9 shows a lug 138 extending radially outwardly from the shaft 80 of the handle 68 such that the lug 138 is coaxially disposed on the translation axis. The lug 138 may be provided at any suitable position on the shaft 80 between the proximal and distal ends 70, 72 of the handle 68. More than one recess 136 may be provided, such as the two recesses positioned on opposing sides of the lug 138. The pawl 134 is dimensioned to be at least partially seated within the recess 136. A biasing element 144 may be provided and operably coupled to the handle 68 and the pawl 134. The biasing element 144, for example, a coil spring or a torsion spring, biases the pawl 134 radially outwardly, thereby exposing the pawl 134 beyond the outer circumference of the lug 138 to engage the ratchet ring 132 in a manner to be described.

Figure 14:
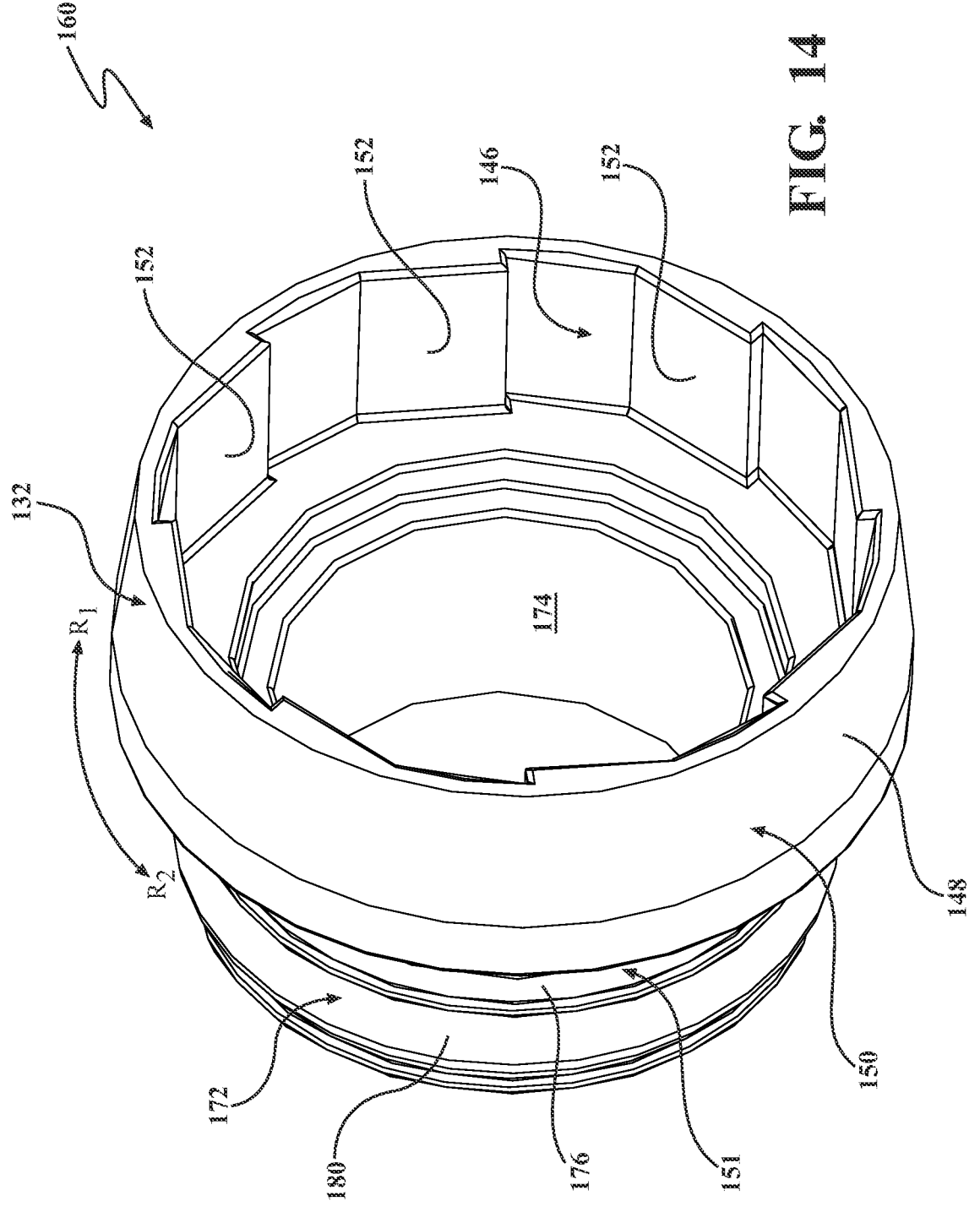
FIG. 14 is a rear perspective view of the defeatable unidirectional mechanism.

The ratchet ring 132 may be coaxially disposed on the translation axis and coaxially aligned with the lug 138 of the handle 68. The ratchet ring 132 is further positioned to encircle the lug 138 such that an inner surface 146 of the ratchet ring 132 is oriented towards the lug 138, and more particularly towards the pawl 134 seated within the lug 138 (see FIGS. 9 and 14). In other words, the ratchet ring 132 is operably coupled to the first control surface 60 at an interface between the inner surface 146 and the pawl 134 coupled to the lug 138. With reference to FIGS. 13 and 14, the ratchet ring 132 includes the inner surface 146 opposite an outer surface 148 and defining a proximal portion 150 of the ratchet ring 132. The ratcheting mechanism includes ratchet teeth 152 circumferentially disposed about the inner surface 146 of the ratchet ring 132. Each of ratchet teeth 152 may be asymmetrical and defined by a trailing edge facing the first direction $(R_1)$ and a leading edge facing the second direction $(R_2)$. With the first torque input provided to the primary control surface 60 in the first direction, the handle 68 and the pawl 134 coupled to the handle 68 rotate in the first direction about the translation axis. The pawl 134, biased towards the inner surface 146 with the biasing element 144, contacts the leading edge of the one of the ratchet teeth 152. Based on the shape of the leading edge (e.g., a ramp-like surface), the pawl 134 is urged away from the inner surface 146 with the biasing element 144 being resiliently deformed as the pawl 134 moves past each of the ratchet teeth 152. Assuming the locking nut 90 is rotatably fixed about the translation axis, the first control surface 60 is rotated with relatively little resistance with corresponding distal advancement of the lead screw 62.

With the second torque input provided to the primary control surface 60 in the second direction, the handle 68 and the pawl 134 coupled to the handle 68 rotate in the second direction about the translation axis until the pawl 134 engages the trailing edge of one of the ratchet teeth 152. The trailing edge of the ratchet 152 and a tip of the pawl 134 are shaped to firmly engage such that the primary control surface 60 cannot be further rotated in the second direction (in the absence of a defeatable mechanism to be described). Thus, the unidirectional torque mechanism 130 is adapted to permit for rotation of the first control surface 60 about the translation axis in the first direction, and generally prevent rotation of the first control surface 60 about the translation axis in the second direction. It is to be understood that the second torque input may originate from the lead screw 62 being urged proximally under the influence of the compressed curable material within the dispensing volume 34. Thus, the unidirectional torque mechanism 130 prevents proximal movement of the lead screw 62 rotatably fixed to the primary control surface 60 (and when the locking nut 90 is rotatably fixed about the translation axis).

Operation of the curable material dispensing system 30 may provide an audible indication and/or a tactile feedback to the physician. The unidirectional torque mechanism 130 may be configured to provide for an impact that may be heard and/or be felt by the hand of the physician holding the handle 68. In one non-limiting example, the biasing element 144 biases the pawl 134 towards the inner surface 146 of the ratchet ring 132. As the pawl 134 passes the trailing edge of each of the ratchet teeth 152 in the first direction, a brief moment occurs where a small gap exists between the pawl 134 and the inner surface 146 with the biasing element 144 being resiliently deformed. In other words, trailing edge of the ratchet teeth 152 may be shaped as a "plateau" relative to the inner surface 146 of the ratchet ring 132. Immediately upon passing the trailing edge at which the biasing element 144 is resiliently deformed, the biasing element 144 urges the pawl 134 towards the inner surface 146, quickly closing the gap. The impact between the pawl 134 and the inner surface 146 may provide the audible indication and/or the tactile feedback to the physician. In other words, the pawl 134 and the ratchet ring 132 may be formed from materials, such as metal or plastic, to provide a "click" as the pawl 134 strikes the inner surface 146 of the ratchet ring 132. Likewise, the pawl 134 strikes the inner surface 146 of the ratchet ring 132 may be with suitable force to be felt by the hand of the physician holding the handle 68.

With continued reference to FIG. 14, the ratchet teeth 152 may be circumferentially spaced equally about the inner surface 146 of the ratchet ring 152. As a result, an angular displacement of rotation of the first control surface 60 about the translation axis may be fixed between each successive audible indication and/or tactile feedback. Provided the locking nut 90 is rotatably fixed about the translation axis during the input of the first torque input to the first control surface 60, the angular displacement between each one of the equally spaced ratchet teeth 152 is associated with a fixed distance of the distal advancement of the lead screw 62 and the plunger 42 along the translation axis. By extension, the fixed distance of the distal advancement of the lead screw 62 and the plunger 42 along the translation axis may be associated with a fixed volume of compressed curable material dispensed from the dispensing volume 34. For example, each successive audible indication and/or tactile feedback may be associated with 0.05, 0.10, 0.25, 0.50, or 1.0 cc being dispensed from the dispensing volume 34. The fixed volume associated with each successive audible indication and/or tactile feedback may be based, at least in part, on circumferential spacing between the ratchet teeth 152, the pitch of the internal threads 92 of the locking nut 90 and the external threads 94 of the lead screw 62, and the like. While the movement of the plunger 42 may also be visible through the chamber 32 when formed from transparent materials, the audible indications and/or tactile feedback being associated with a fixed volume of curable material provides supplemental means for the physician to assess the amount of the curable material being dispensed from the system 30.

Alternatively, the unidirectional torque mechanism 130 may not include the biasing element 144 biasing the pawl 134 towards the inner surface 146 of the ratchet ring 132. The pawl 134 may be formed from resilient, semi-rigid, and/or shape memory material(s) (e.g., Nitinol) adapted to deflect under the forces from the ratchet teeth 152 as the pawl 134 moves past each of the ratchet teeth 152, then return to an original shape (in contact with the inner surface 146) after passing the trailing edge of the ratchet teeth 152 in the first direction. It should be also be appreciated that the ratchet ring may have alternative shapes and configurations other than what is shown, such as a polygonal shape. In certain implementations, the unidirectional torque mechanism 130 may be an overrunning clutch with a driver wheel adapted to be in engagement with a driven wheel. Other constructions of imparting unidirectional rotation between two structures may be implemented into the system of the present disclosure.

As previously described in detail, the curable material dispensing system 30 includes the safety feature of providing for proximal movement of the lead screw 62 along the translation axis in response to the actuator 120 being in the disengaged position. In implementations where the biasing member 128 biases the second control surface 122 away from the locking nut 90 (i.e., biases the second control surface such that the actuator is in the disengaged position), the safety feature can be activated by merely releasing the lever 126 with the lever 126 or other control surface acting as a so-called "dead man's switch." Yet for any number of reasons, the physician may wish to provide for proximal movement of the lead screw 62 along the translation axis, for example, in addition to the proximal movement associated with the release of the "dead man's switch." It is readily appreciated that the threads 92, 94 typically would provide for proximal movement of the lead screw 62 along the translation axis but for the unidirectional torque mechanism 130.

The curable material dispensing system 30 may include a defeatable unidirectional mechanism 160. The defeatable unidirectional mechanism 160 may operably couple the first control surface 60 and the housing 50. The defeatable unidirectional mechanism 160 permits proximal movement of the lead screw 62 in response to the first control surface 60 receiving the second torque input exceeding a torque threshold. By extension, the defeatable unidirectional mechanism 160 prevents for the proximal movement of the lead screw 62 when the second torque input does not exceed the torque threshold. In a practical sense, the defeatable unidirectional mechanism 160 is configured to prevent the rotation of the handle 68 in the second direction when the lead screw 62 is urged proximally under the influence of the compressed curable material within the dispensing volume 34 (e.g., when the physician resets his or her hand), but permit the rotation of the handle 68 in the second direction from the physician deliberating applying sufficient torque to the primary control surface 60, which would result in the proximal movement of the lead screw 62. It is to be understood that the torque threshold may be based primarily on a frictional relationship defining a clutch mechanism (generally referred to as 172) to be described, but also may further be based on friction between the internal and external threads 92, 94, the forces provided by the compressed curable material, and the like. Consequently, the torque threshold may be specifically designed (based on the characteristics of the clutch mechanism 172) such that the typical torque on the handle 68 from only the lead screw 62 being backdriven and urged proximally is less than the torque threshold.

The defeatable unidirectional mechanism 160 may be configured to permit for the distal advancement of the lead screw 62 in response to the first control surface 60 receiving the first torque input less than the torque threshold. In other words, in the first direction, the handle 68 may be easily rotatable at a torque relatively less than that required to rotate the handle 68 in the second direction (e.g., as the pawl 143 moves passed the teeth 152 in the first direction). It is understood that as the curable material becomes increasingly compressed within the dispensing volume 34, the first torque input required to distally advance the lead screw 62 (against the forces from the compressed curable material) may increase beyond the torque threshold.

Referring now to FIGS. 3-5, 13 and 14, the defeatable unidirectional mechanism 160 may include the unidirectional torque mechanism 130 previously described. In other words, the unidirectional torque mechanism 130 may be a functional component of the defeatable unidirectional mechanism 160. With concurrent reference to FIG. 8, the unidirectional torque mechanism 130 is positioned in the frictional relationship with the chamber mount 44 that is fixed relative to the housing 50, and the clutch mechanism 172 may be defined at the frictional interface (e.g., the unidirectional torque mechanism 130 "slips" relative to the chamber mount 44). The clutch mechanism 172 is configured to permit rotation of the ratchet ring 132 (operably coupled to the first control surface 60) in the first and second directions when the ratchet ring 132 receives a torque input exceeding the torque threshold sufficient to overcome the frictional relationship.

Figure 12:
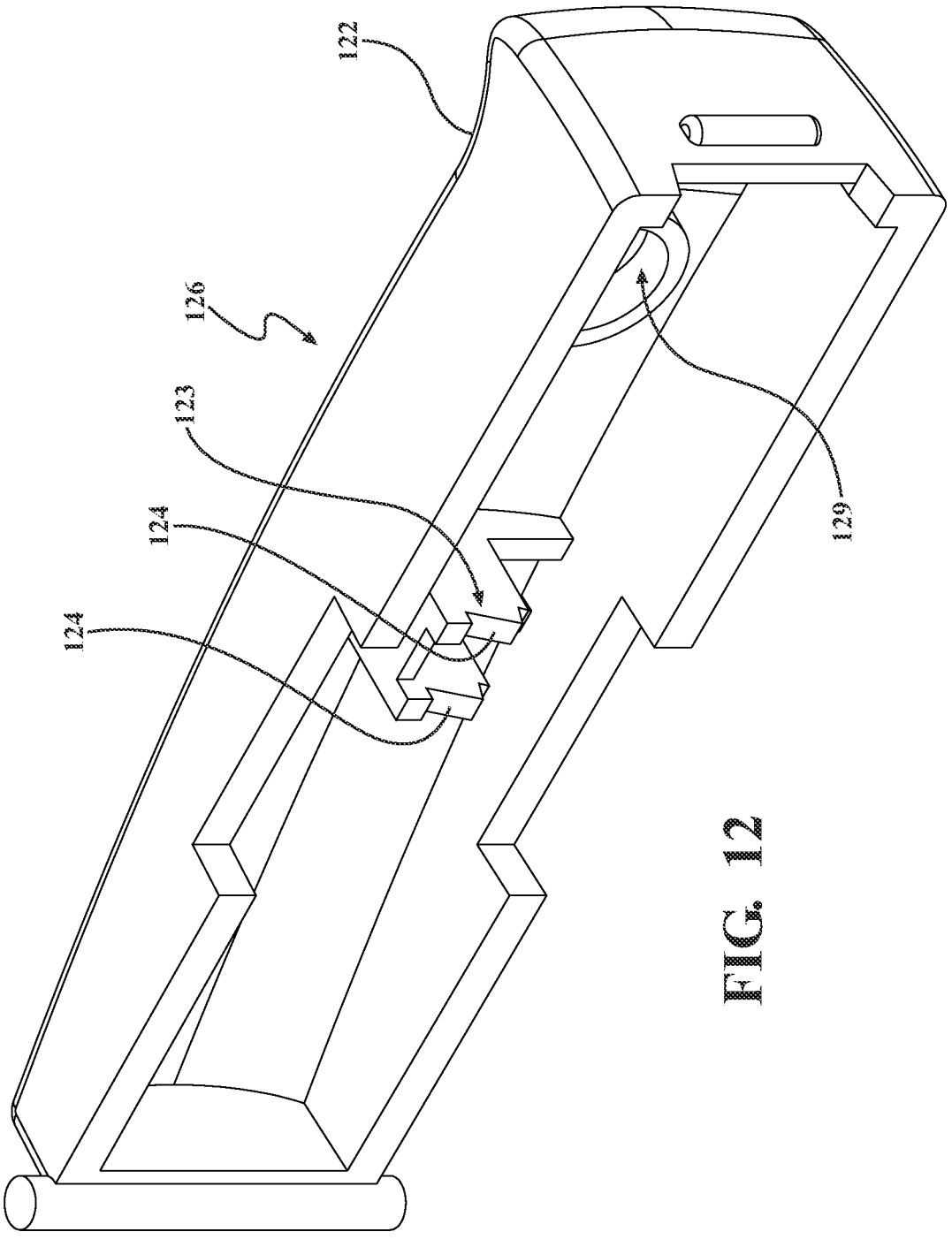
FIG. 12 is a bottom perspective view of an actuator including a second control surface.

The ratchet ring 132 includes the inner surface 146 opposite the outer surface 148 to define the proximal portion 150 of the ratchet ring 132. The ratchet ring 132 may also includes a distal portion 151 coupled to the proximal portion 150. The distal portion 151 is positioned distally the proximal portion 150 and along the translation axis. Similar to the proximal portion 150, the distal portion 151 may be generally ring-shaped and defined between an inner annular surface 174 and an outer annular surface 176, as shown in FIGS. 12, 13 and 15. The outer annular surface 176 of the distal portion 151 may be in the frictional relationship with the chamber mount 44 to define the clutch mechanism 172. One or more frictional elements 180 may be provided at the interface between the outer annular surface 176 and an inner surface of the proximal ring 49 of the chamber mount 44 (see FIGS. 3-5 and 8) to increase the frictional relationship to achieve a desired torque threshold. In other words, if a relatively greater frictional relationship is associated with the clutch mechanism 172, the physician is required to provide a larger second torque input to the first control surface 60 to overcome the frictional relationship and move the lead screw 62 in the proximal direction along the translation axis. FIGS. 13 and 14 show the frictional elements being an O-ring disposed within a recess within the outer annular surface 176 of the distal portion 151. More than one O-ring may be provided. The O-ring(s) have a thickness slightly greater than a depth of the recesses in order to contact the inner surface of the chamber mount 44.

The clutch mechanism 172 is configured to permit rotation of the first control surface 60 in the first and second directions in response to receiving the first and second torque inputs, respectively, exceeding the torque threshold, and the unidirectional torque mechanism 130 is adapted to permit for rotation of the first control surface 60 in the first direction, and prevent rotation of the first control surface 60 about the translation axis in the second direction. Thus, with the unidirectional torque mechanism 130 and the clutch mechanism 172 functionally integrated, the first control surface 60 may be rotatable in the first direction when the first torque input is below the torque threshold.

A first magnitude of the first torque input is required to be provided to the primary control surface 60 to overcome the force of the biasing members 128 biasing the pawl 134 as the pawl 134 passes the ratchet teeth 152 in the first direction, along with the forces associated with the curable material compressed within the dispensing volume 34. A second magnitude of the first torque input defines the torque threshold associated with the clutch mechanism 172. The first magnitude is less than the second magnitude. In other words, the frictional engagement defining the clutch mechanism 172 should never be overcome as the handle 68 is rotated in the first direction, since the pawl 134 is configured to much more easily move past the ratchet teeth 152. In the second direction, however, the tip of the pawl 134 firmly engages the ratchet teeth 152, and increasing application of the second torque input is insufficient to overcome the engagement. The second torque input is effectively transferred from the handle 68, to the pawl 134, then to the ratchet teeth 152 of the ratchet ring 132. With continued increasing application of the second torque input, eventually the second torque input exceeds the torque threshold such that the frictional engagement of the clutch mechanism 172 is overcome and the ratchet ring 132 rotates relative to the chamber mount 44, and thus relative to the housing 50. The torque threshold may be two, three, five or time times greater than the first torque input required to rotate the handle 68 in the first direction. With the locking nut 90 in the engaged position, the second torque input above the torque threshold causes the lead screw 62 to move in the proximal direction relative to the locking nut 90. The above disclosure delineates that the defeatable unidirectional mechanism 160 is advantageously configured to provide for the distal advancement of the lead screw 62 with the first torque input less than the torque threshold; prevent for the proximal movement of the lead screw 62 with the second torque input less than the torque threshold; and permit for the proximal movement of the lead screw 62 with the second torque input exceeding the torque threshold. Consequently, with the actuator 120 engaging the locking nut 90, the physician may distally advance the plunger 42 within the dispensing volume 34 by rotating the handle 68 in the first direction with relative ease. The physician may release his or her hand to reset it (or for any other reason), and the handle 68 is prevented from rotating in the second direction by the defeatable unidirectional mechanism 160. The physician may cause the proximal movement of the plunger 42 in two ways: releasing the secondary input force to the second control surface 122, and/or rotating the handle 68 in the second direction with relative effort to overcome the frictional relationship.

In an alternative implementation, at least a portion of the defeatable unidirectional mechanism 160 may be rotatably fixed relative to the housing 50. For example, the defeatable unidirectional mechanism 160 may include a friction ring is rotatably fixed relative to the housing 50 with the first control surface 60 is movable (e.g., rotatable) relative to the friction ring. In another alternative implementation, the trailing edge of the ratchet teeth 152 and the tip of the pawl 134 are complimentarily shaped so as to cause defeatable engagement such that the primary control surface 60 can be rotated in the second direction when the second torque input exceeds the torque threshold.

Figure 16:
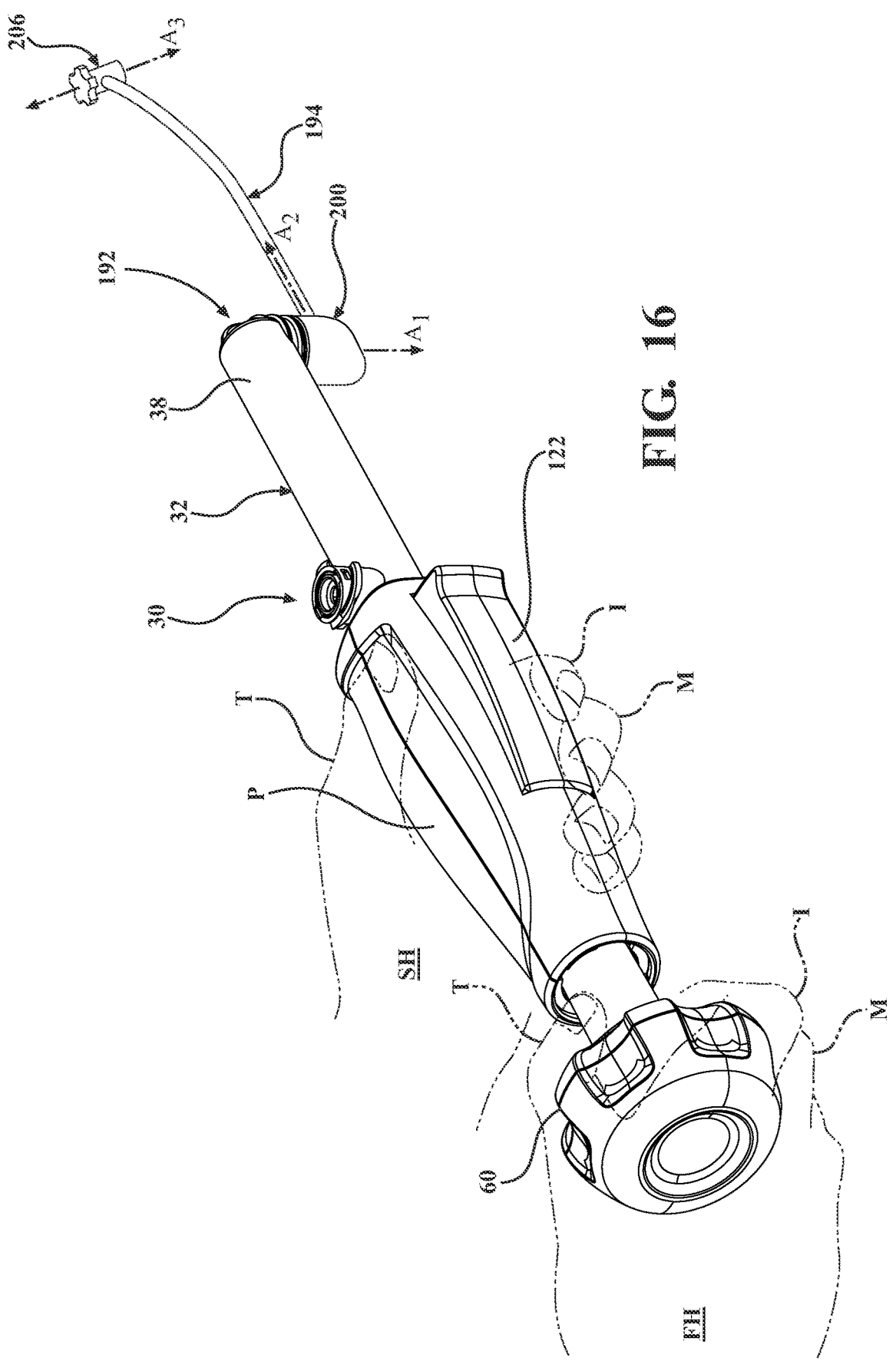
FIG. 16 shows the curable material dispensing system with the extension tube in a deployed configuration during use.

In view of the foregoing description of the curable material dispensing system 30, methods of operating the system 30 are provided with reference to FIG. 16. The system 30 may be operated by the physician including first hand (FH) and second hand (SH) each includes a palm (P) and an index finger (I), a middle finger (M), and a thumb (T) extending from the palm (see FIG. 21). The housing 50 may be supported in the palm of the second hand of the physician. The secondary input force is applied to the second control surface 122 to move the second control surface 122 from the disengaged position to the engaged position. The secondary input force may be provided while the second hand supports the housing 50, such as with the index finger, middle finger, and/or the thumb of the second hand. The actuator 120 is moved into engagement with the locking nut 90 to prevent rotation of the locking nut 90 about the translation axis. The second control surface 122 is maintained in the engaged position against a force provided by the biasing member 128. The second control surface 122 with the index finger, middle finger, and/or the thumb of the second hand while supporting the primary control surface 60 with the first hand.

With the second control surface maintained in the engaged position, the primary input force is provided to the first control surface 60. The primary input force may be rotation provided by the index finger, middle finger, and/or the thumb of the first hand. The unidirectional torque mechanism permits the distal movement of the lead screw 62 with rotation of the first control surface 60 about the translation axis in the first direction with relative ease. The lead screw 62 moves distally along the translation axis to compress the curable material within the dispensing volume 34. The physician may remove the secondary input force provided to the second control surface 122. In particular, the index finger, middle finger and/or the thumb of the second hand may be removed from the second control surface 122 while supporting the housing 50 with the palm of the second hand, and while supporting the first control surface 60 with the first hand. The biasing member 128 resiliently moves the second control surface 122 from the engaged position to the disengaged position. The actuator 120 is moved out of engagement with the locking nut 90. The locking nut 90 is now rotatable about the translation axis and provides for movement of the lead screw 62 in the proximal direction along the translation axis to permit the compressed curable material to at least partially decompress within the dispensing volume 34.

According to another exemplary method of the curable material dispensing system 30, the actuator 120 is initially biased into engagement with the locking nut 90 with a force provided by the biasing member 128. In other words, without the secondary input force provided to the second control surface 122, the locking nut 90 is rotatably fixed about the translation axis. The primary input force is provided to the first control surface 60 while the locking nut 90 is rotatably fixed with the actuator 120 in the engaged position. The secondary input force is applied to the second control surface 122 with the secondary input force being sufficient to overcome the force provided by the biasing member 128 and move the actuator 120 to the disengaged position. The locking nut 90 is now rotatable about the translation axis and provides for movement of the lead screw 62 in the proximal direction along the translation axis to permit the compressed curable material to at least partially decompress within the dispensing volume 34. The secondary input force may be released from the second control surface 122, after which the biasing member 128 returns the actuator 120 to the engaged position with the locking nut 90. The threadable engagement between the internal threads 92 of the locking nut 90 and the external threads 94 of the lead screw provide for translation of the lead screw 62 distally along the translation axis to compress the curable material within the dispensing volume 34. The compressed curable material is dispensed from the distal outlet 38 of the chamber 32 in communication with the dispensing volume 34.

With continued reference to FIG. 16 and further reference to FIG. 1, as previously mentioned, the extension tube 190 may be coupled to the distal coupler 46 of the chamber 32. The extension tube 190 is adapted to be coupled to the surgical instrument secured within the patient, such as the access cannula penetrating bony anatomy. The extension tube 190 includes the elbow coupler 192, and a flexible tube 194 rotationally and/or pivotally coupled to the elbow coupler 192. The flexible tube 194 may be formed from flexible tubing, but it is contemplated that the flexible tube 194 may be of suitably rigid construction. It should be further appreciated that the components of the extension tube 190 are constructed so as to withstand pressures associated with dispensing the compressed curable material. For example, the extension tube 190 is constructed to withstand pressures of 200, 500, 1000, 3000, or 5000 or more pounds per square inch (psi).

The elbow coupler 192 may be adapted to removably couple with the distal coupler 46 of the curable material dispensing system 30. With the elbow coupler 192 coupled to the distal coupler 46, the elbow coupler 192 is in fluid communication with the distal outlet 38 and the dispensing chamber 32 of the system 30. The elbow coupler 192 may be a relatively short, tubular or hollow structure that is rigid in construction. The flexible tube 194 is coupled to elbow coupler 192 to establish fluid communication between the flexible tube 194 and the dispensing chamber 32 of the system 30.

The elbow coupler 192 is configured to articulate the flexible tube 194 relative to the elbow coupler 192 about a first axis $A_1$, and the rotating coupler 200 is configured to articulate the flexible tube 194 relative to the elbow coupler 192 about a second axis $A_2$, as shown in FIG. 16. The second axis $A_2$ may be orthogonal to the first axis $A_1$. Thus, with the flexible tube 194 in the manner described, the flexible tube 194 is articulable relative to the system 30 in at least two degrees of freedom (e.g., pivotable about the first axis $A_1$ and rotatable about the second axis $A_2$). The extension tube 190 further includes a cannula coupler 206 coupled to the flexible tube 194. The cannula coupler 206 is adapted to be removably coupled to the surgical instrument secured within the patient, for example, the access cannula, an interior of the bony anatomy is in fluid communication with the dispensing chamber 32 of the system 30. For example, during a vertebroplasty procedure, the curable material may be dispensed the extension tube 190, through the access cannula, and into the cancellous region of the vertebral body. The cannula coupler 206 is configured to rotate about a third axis $A_3$, as illustrated in FIG. 16. Thus, the extension tube 190 of the present disclosure provides for articulation of the curable material dispensing system 30 relative to the surgical instrument rigidly secured within the patient in at least three degrees of freedom (e.g., pivotable about the first axis $A_1$, rotatable about the second axis $A_2$, and rotatable about the third axis $A_3$). Moreover, additional "quasi" degrees of freedom may be realized by the flexibility of the flexible tube 194 (i.e., the physician may reorient the system 30 relative to the surgical instrument by causing bending of the flexible tube 194 despite not having another "true" degree of freedom (e.g., prismatic joint). The extension tube 190 of the present disclosure advantageously provides the physician with improved maneuverability about the patient and the surgical site without placing undue stress on the surgical instrument rigidly secured within the patient. Further, in procedures where fluoroscopy is utilized, the physician is better able to maintain fluid communication between the system 30 and the interior the bony anatomy while avoiding unnecessary exposure to radiation. For example, the several degrees of freedom afforded by the extension tube 190 permits the physician to be separated from the surgical field by a screen while maintain control of the system 30 coupled to the patient.

Figure 17:
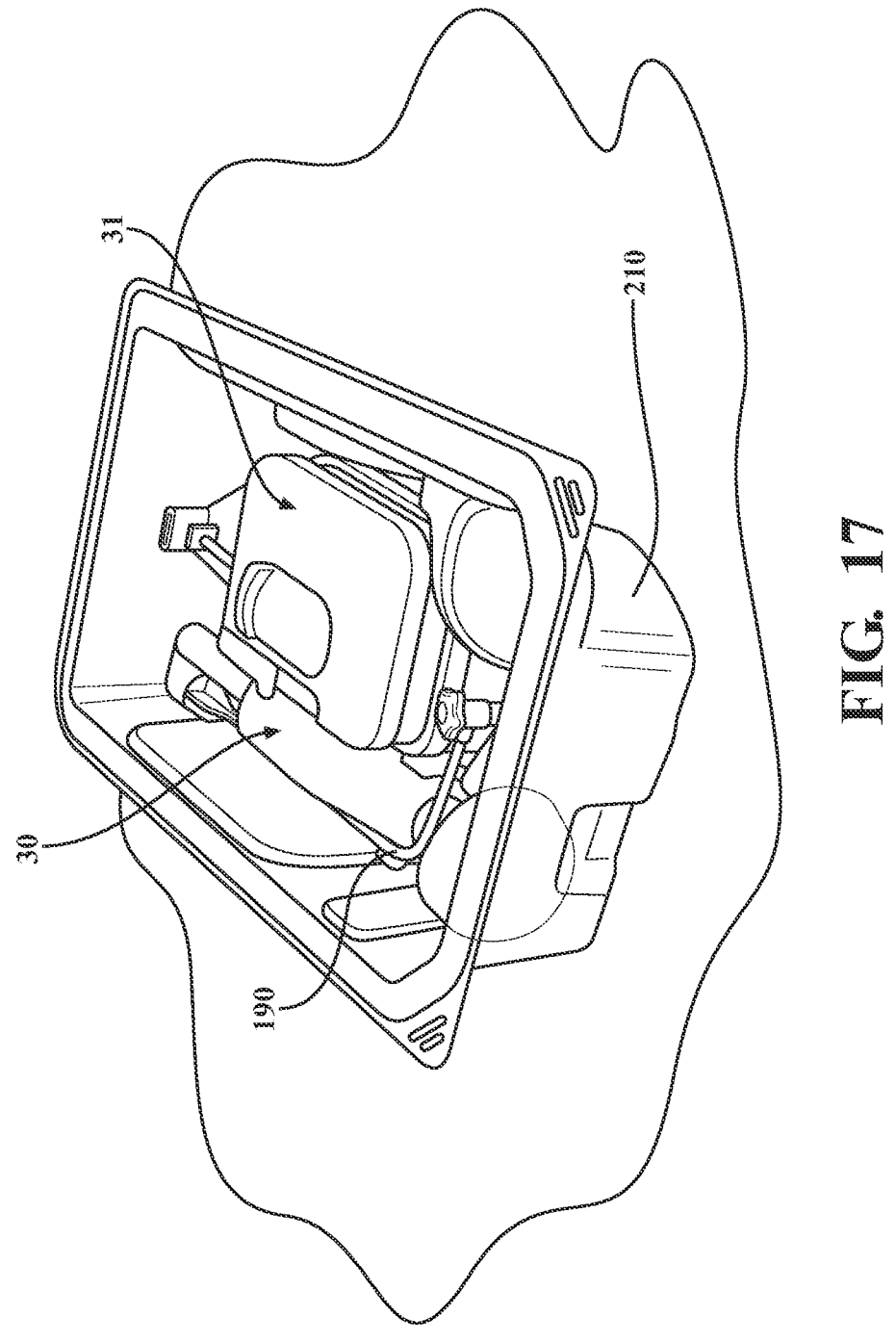
FIG. 17 is a schematic representation of the curable material dispensing system, the mixing and compression system, and the extension tube in a packaging configuration being disposed within packaging.

A further advantage of the extension tube 190 of the present disclosure is realized during packaging, shipping, and/or storing of the system 30. Known systems may require a flexible tube be installed on a dispensing system immediately prior to use, which consumes time and resources that could be diverted to other tasks associated with the surgical procedure. Alternatively, for flexible tubes preinstalled on the dispensing system, the packaging must be sufficiently large to accommodate the structures. Likewise, storage of the packaged dispensing system consumes an inordinate amount of space in, for example, a storage room. In either instance, the dispensing system with the flexible tubing consumes a substantial amount of tabletop space within the surgical suite and, more particularly, a large amount of space within the sterile field. The extension tube 190 of the present disclosure provides for a system and/or method of packaging the curable material dispensing system 30. FIG. 17 shows a schematic representation of the curable material dispensing system 30, the mixing and compression system 31, and the extension tube 190 within packaging 210. With concurrent reference to FIG. 5, it is observed that the distal coupler 46 is at an angle, and in particular a right angle, relative to the chamber 32 oriented on the translation axis. Likewise, the elbow coupler 192, as implied by its name, orients the flexible tube 194 at an angle relative to the coupling interface between the elbow coupler 192 and the distal coupler 46. The resulting arrangement, shown in FIGS. 1 and 17, allows the flexible tube 194 to be articulated to a packaging configuration in which the chamber 32 of the curable material dispensing system 30 and the flexible tube 194 are substantially parallel. The extension tube 190 and the curable material dispensing system 30 are may be coupled to one another prior to packaging to be nestled closely to one another within the packaging 210 while providing the flexible tube 194 of sufficient length without requiring undesirably large packaging.

The curable material dispensing system 30 is provided, and the elbow coupler 192 is coupled to the distal coupler 46 of the chamber 32, thereby establishing fluid communication between the cannula coupler 206 and the dispensing volume 34. The extension tube 190 may be considered in a deployed configuration in which the chamber 32 and the elbow coupler 192 are substantially parallel and the flexible tube 194 is positioned away the dispensing volume 34 relative to the elbow coupler 196. The deployed configuration is shown in FIG. 16. In the deployed configuration the elbow coupler 192 and the flexible tube 194 may be offset. The flexible tube 194 is articulated about the elbow coupler 196 from the deployed configuration to the aforementioned packaging configuration in which the elbow coupler 192 and the flexible tube 194 are substantially parallel and the flexible tube 194 is positioned towards the dispensing volume 34 relative to the elbow coupler 196. The packaging configuration is shown in FIG. 1. In the packaging configuration, the flexible tube 194 may be positioned adjacent the housing 50. Thereafter, the curable material dispensing system 30 and the extension tube 190 in the packaging configuration are positioned within the packaging 210 having dimensions sufficient to accommodate the curable material dispensing system 30 and the extension tube 190. The packaging 210 may be a plastic housing that allows sterilant to enter and contact the various surfaces of the curable material dispensing system 30 and the extension tube 190. The packaging 210 may be configured to maintain sterility of the curable material dispensing system 30 and the extension tube 190 disposed therein (e.g., hermetically sealed).

The extension tube 190 may remain in the packaging configuration after removal from the packaging 210. Several benefits are realized with situating the curable material dispensing system 30 within the surgical suite with the extension tube 190 in the packaging configuration. Whether situated on a "back table" or a Mayo stand of the surgical suite, the curable material dispensing system 30 consumes significantly less space within the sterile field, space that may be reallocated to other surgical instruments and items required to be in the sterile field. Further, in practice known systems were often situated on the back table and Mayo stand with the flexible tubes extending over a perimeter of the table or stand. The portion of the flexible tube extending outside the sterile zone increases the risk of contact with unsterile objects, and increases the risk of being inadvertently knocked off the table or stand by personnel moving about the surgical suite. The curable material dispensing system 30 with the extension tube 190 of the present disclosure overcomes the aforementioned disadvantages. And once the dispensing chamber 32 receives the curable material and the system 30 is ready for use during the surgical procedure, the extension tube 190 may be quickly moved from the packaging configuration to the deployed configuration.

As described throughout the present disclosure, one of the many advantageous features of the system 30 includes minimizing or eliminating the likelihood of drool. In certain instances it may be desirable to provide a secondary mechanism for further minimizing or eliminating the likelihood of drool. In certain implementations, the curable material dispensing system 30 may include a flow diverter and a drool accumulator (not shown) to be described. Examples of the flow diverter and the drool accumulator suitable for the present application are disclosed in commonly owned PCT Application No. PCT/US2018/019211, filed on Feb. 22, 2018, the contents of which are incorporated by reference in its entirety. The flow diverter and drool accumulator may be coupled to the extension tube 190 opposite the chamber 32. A first diverter outlet is configured to be coupled to an access cannula positioned within the patient (e.g., penetrating bony an anatomy) to selectively dispense the curable material to a target site, and a reservoir is in fluid communication with a second diverter outlet. A valve is provided and arranged for selective movement between a first configuration in which fluid communication is established between the dispensing volume 34 and the reservoir, and fluid communication is interrupted between the dispensing volume 34 and the first diverter outlet, and a second configuration of the valve, fluid communication is established between the dispensing volume 34 and the first diverter outlet, and fluid communication is interrupted between the dispensing volume 34 and the reservoir. Should it be desirable to direct the curable material received within the drool accumulator towards the target site, a plunger or other mechanism may be actuated by the user. Thus, in one implementation, a system for dispensing curable material includes: a chamber defining a dispensing volume adapted to dispense the curable material through a distal outlet in communication with the dispensing volume; a first control surface adapted to receive a primary input force from a user; a lead screw rotatably fixed relative to the first control surface with the lead screw includes a proximal end, a distal end, external threads at least partially disposed between the proximal and distal ends, and a translation axis defined between the proximal and distal ends; a plunger coupled to the lead screw with the plunger disposed within the dispensing volume and adapted to be advanced distally along the translation axis to compress the curable material within the dispensing volume in response to the first control surface receiving the primary input force; an extension tube coupled to the chamber with the extension tube defining a lumen in fluid communication with the dispensing volume; a flow diverter includes an inlet coupled to the extension tube opposite the chamber, a first diverter outlet, a second diverter outlet with each of the first and second diverter outlets in fluid communication with the lumen of the extension tube, wherein the flow diverter is adapted to be coupled to and in fluid communication with a delivery cannula for directing the curable material to a target site; and a drool accumulator defining a reservoir for receiving residual amounts of the curable material with the drool accumulator defines a reservoir in fluid communication with the second diverter outlet and the reservoir.

The foregoing description is not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention claimed is:

1. A system for dispensing curable material, the system comprising:
    a housing;
    a chamber coupled to the housing and defining a dispensing volume;
    a first control surface coupled to the housing;
    a lead screw rotatably fixed relative to the first control surface and adapted to be translated to compress the curable material within the dispensing volume; and
    a defeatable unidirectional mechanism operably coupling the first control surface and the housing, wherein the defeatable unidirectional mechanism is adapted to (i) permit for distal advancement of the lead screw with rotation of the first control surface in a first direction from a first torque input that is below a torque threshold, (ii) prevent rotation of the first control surface in a second direction opposite the first direction from a second torque that is below the torque threshold, and (iii) permit for proximal movement of the lead screw with rotation of the first control surface in the second direction from a third torque input that is at least equal to the torque threshold, wherein the defeatable unidirectional mechanism is positioned in a frictional relationship with the housing with the torque threshold being of a magnitude to overcome the frictional relationship, and wherein the defeatable unidirectional mechanism further comprises a ring, and a frictional element engaging each of an outer surface of the ring and an inner surface of the housing.

2. The system of claim 1, wherein the ring is a ratchet ring comprising a proximal portion and a distal portion, wherein ratchet teeth are circumferentially disposed about an inner surface of the proximal portion, and wherein the frictional element is disposed within a recess defined by the distal portion.

3. The system of claim 2, wherein the frictional element is an O-ring having a thickness greater than a depth of the recess.

4. The system of claim 1, further comprising a pawl operably coupled to the first control surface, wherein the ring is a ratchet ring comprising ratchet teeth circumferentially disposed about an inner surface of the ratchet ring and configured to be engaged by the pawl.

5. The system of claim 4, further comprising a biasing element biasing the pawl towards the inner surface of the ratchet ring.

6. The system of claim 4, wherein the ratchet teeth are circumferentially spaced equally about the inner surface such that an angular displacement of the first control surface in the first direction between successive ones of the ratchet teeth is associated with a fixed distance of the distal advancement of the lead screw.

7. The system of claim 1, further comprising a handle comprising a grip portion including the first control surface, and a shaft extending from the grip portion and defining a lumen, wherein the lead screw is axially movable within the shaft of the handle.

8. The system of claim 7, wherein the shaft further defines a slot forming at least a portion of the lumen, wherein the lead screw comprises a ridge extending longitudinally along the lead screw, wherein engagement between the ridge and the slot is configured to prevent relative rotation and permit relative axial movement between the lead screw and the handle.

9. The system of claim 1, further comprising a locking nut disposed rotatably within the housing and comprising internal threads, wherein the lead screw comprises external threads configured to engage the internal threads of the locking nut to convert rotation of the lead screw into translation of the lead screw.

10. The system of claim 1, wherein the second torque is based on forces from the curable material being compressed within the dispensing volume, and wherein the first and third torques inputs are an input from a user.

11. A system for dispensing curable material, the system comprising:
    a housing;
    a chamber coupled to the housing and defining a dispensing volume;
    a first control surface coupled to the housing;
    a lead screw rotatably fixed relative to the first control surface and adapted to compress the curable material within the dispensing volume based on distal advancement of the lead screw with rotation of the first control surface in a first direction; and
a defeatable unidirectional mechanism operably coupling the first control surface and arranged in a frictional relationship with the housing, wherein the defeatable unidirectional mechanism is configured to prevent rotation of the first control surface in a second direction opposite the first direction from a first torque input that is below a torque threshold to overcome the frictional relationship, and permit for proximal movement of the lead screw with rotation of the first control surface in the second direction from a second torque input that is at least equal to the torque threshold to overcome the frictional relationship,
    wherein the defeatable unidirectional mechanism further comprises a ring, and a frictional element engaging each of an outer surface of the ring and an inner surface of the housing.

12. The system of claim 11, wherein the ring is a ratchet ring comprising a proximal portion and a distal portion, wherein ratchet teeth are circumferentially disposed about an inner surface of the proximal portion, and wherein the frictional element is disposed within a recess defined by the distal portion.

13. The system of claim 12, wherein the frictional element is an O-ring having a thickness greater than a depth of the recess.

14. The system of claim 12, further comprising a pawl operably coupled to the first control surface, wherein engagement between the pawl and one of the ratchet teeth is configured to cause rotation of the ratchet ring relative to the housing in the second direction based on the second torque input exceeding the torque threshold.

15. A method for operating a curable material dispensing system including a housing, a chamber coupled to the housing and defining a dispensing volume, a first control surface, a lead screw rotatably fixed to the first control surface, a second control surface, a biasing member engaging the second control surface, and a defeatable unidirectional mechanism including a ring positioned in a frictional relationship with an inner surface of the housing, the method comprising the steps of:
    maintaining the second control surface in an engaged position against a force provided by the biasing member;
    applying a first torque input to the first control surface in a first direction to cause distal movement of the lead screw to compress the curable material within the dispensing volume;
    removing the first torque input, wherein a second torque on the first control surface in a second direction opposite the first direction is below a torque threshold, and wherein rotation of the first control surface in the second direction is prevented by the defeatable unidirectional mechanism; and
    applying a third torque input to the first control surface in the second direction and above the torque threshold in which a magnitude of the third input torque overcomes the frictional relationship, wherein rotation of the first control surface in the second direction is permitted by the defeatable unidirectional mechanism and causing proximal movement of the lead screw to decompress the curable material within the dispensing volume.

16. The method of claim 15, wherein the second control surface is maintained in the engaged position while per-forming the steps of applying the first torque input, removing the first torque input, and applying the third torque input.

* * * * *